(12) United States Patent
Danishefsky et al.

(10) Patent No.: US 7,910,623 B2
(45) Date of Patent: Mar. 22, 2011

(54) SYNTHESIS OF SCABRONINES AND ANALOGUES THEREOF

(75) Inventors: Samuel J. Danishefsky, Englewood, NJ (US); Stephen P. Waters, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 193 days.

(21) Appl. No.: 12/017,951

(22) Filed: Jan. 22, 2008

(65) Prior Publication Data

US 2011/0009485 A9    Jan. 13, 2011

(51) Int. Cl.
*A61K 31/21*    (2006.01)
*C07C 69/74*    (2006.01)

(52) U.S. Cl. .................. 514/510; 560/117; 562/499

(58) Field of Classification Search .................. 560/117; 562/499; 514/510
See application file for complete search history.

(56) References Cited

U.S. PATENT DOCUMENTS

| | | | |
|---|---|---|---|
| 4,629,700 | A | 12/1986 | Prevatt et al. |
| 6,683,087 | B2 | 1/2004 | Wikstrom et al. |
| 2005/0032802 | A1 | 2/2005 | Lavallee et al. |

FOREIGN PATENT DOCUMENTS

| | | |
|---|---|---|
| JP | 7-069961 | 3/1995 |
| JP | 11-269125 | 10/1999 |
| JP | 2002-234896 | 8/2002 |
| JP | 2003-089670 | 3/2003 |

OTHER PUBLICATIONS

Honda et al., 2005, CAS: 314540.*
Yus et al., 2005, CAS: 143:305679.*
Berge, et al., J. Pharmaceutical Sciences, 66: 1-19, 1977.
Birman et al. J. Am. Chem. Soc. 2002, 124, 2080.
*Brain Res.* 570:316-22, 1990.
Buchschacher, et al., *J. Org. Syn., Coll.*vol. VII 1990, 368.
Cho et al. J. Am. Chem. Soc. 2004, 126, 14358.
Ciceri et al. Tetrahedron Lett. 1997, 38, 389.
Corey et al. J. Am. Chem. Soc. 1961, 83, 1251.
Dawbarn et al. Neuropath. Appl. Neurobiol. 29:211, 2003.
Guerrero et al. Tetrahedron Lett. 1990, 31, 1873.
Hefti et al. Annu. Rev. Pharmacol. Toxicol. 37:239, 1997.
Kirik et al. Nat. Neurosci. 7:105, 2004.
Kita et al. *Tetrahedron* 54:11877, 1998.
Ling et al. J. Org. Chem. 2001, 66, 8843.
Luu et al. *Molecules* 5:1439, 2000.
McMurry et al. Tetrahedron Lett. 1983, 24, 979.
Nagata et al. J. Am. Chem. Soc. 1972, 94, 4644.
Obara et al. Mol. Pharmacol. 59:1287, 2001.
Pellissier, H. *Tetrahedron* 2005, 61, 6479.
Pettus et al. J. Am. Chem. Soc. 2000, 122, 6160.
Piers, et al., *Org. Lett.* 2000, 2, 1407.
Scott et al. J. Am. Chem. Soc. 1986, 108, 3033.
Snider, et al., *J. Am. Chem. Soc.* 1998, 118, 7644.
Stork et al. J. Am. Chem. Soc. 1965, 87, 275.
Takano, *Org. Lett.* 2004, 6, 4897.
Trost, et al., *J. Am. Chem. Soc.* 2005, 127, 2844.
Williams et al. Tetrahedron Lett. 1995, 36, 5461.
Yu et al. Tetrahedron Lett. 2001, 42, 369.
Ward et al., "Synthetic Studies on Cyathin Diterpenes -Total Synthesis of (+/-)-allocyathin B3," Can. J. Chem. 2004, 82, 254-258.
International Search Report for PCT/US06/28155, mailed Jan. 17, 2008.

* cited by examiner

*Primary Examiner* — Rei-tsang Shiao
(74) *Attorney, Agent, or Firm* — Brenda Herschbach Jarrell; Kristen C. Buteau; Choate, Hall & Stewart LLP

(57) ABSTRACT

A novel synthesis of scabronines, which are related to a broader class of angularly fused tricyclic diterpenoids known as cyathanes, is provided. Scabronine G, its methyl ester derivative, and other analogs have been shown to have neurotrophic activity. Therefore, these compounds are particularly useful in treating neurodegenerative diseases such as Alzheimer's disease, Parkinson's disease, Huntington's diseases, etc. The invention provides for the synthesis of scabronines as well as analogs thereof. Pharmaceutical compositions and method of using the inventive compounds are also provided.

61 Claims, 10 Drawing Sheets

Key: (a) Li/NH3, *t*-BuOH, THF, -78 °C; NCCO2Me, 72%; (b) NaH, PhNTf2, DME, 98%; (c) Pd(PPh3)3,Bu3SnH, LiCl, THF, 55 °C, 91%; (d) LHMDS, Me(OMe)NH,HCl, THF, -10 °C, 79%; (e) vinylMgBr, THF, -10 °C, 84%; (f) FeCl3,CH2Cl2, 72%; (g) Et2AlCN, THF, Et3N, TMSCl; (h) *t*-BuOK, THF, -78 °C, *N*-(5-chloro-2-pyridyl)triflimide, 86% over two steps; (i) *i*-PrMgCl, ZnCl2, LiCl, (dppf)PdCl2, THF, 55 °C, 75%; (j) DIBAL-H, CH2Cl2, -78 °C, 88%; (k) NaClO2, NaH2PO4, *t*-BuOH/H2O; (l) MeI, K2CO3, DMF; (m) THF, HCl/H2O; 92% over three steps.

Key: (a) NaH, HCO2Me, DME, 97%; (b) n-PrSH, TsOH, PhH, 50 °C, 93%; (c) n-BuLi/MeOCH2SPh, THF, -78 °C; (d) HgCl2, HCl/MeCN, 80 °C, 86% over two steps; (e) DBU, benzene, 75 °C, quant; (f) TsOH, HO(CH2)2OH, PhH, 89%; (g) aq. NaOH, MeOH, 55 °C, then HCl, 87%.

FIGURE 5A
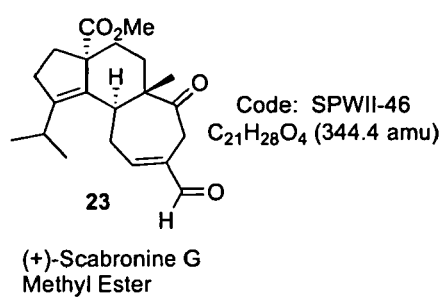
Code: SPWII-46
$C_{21}H_{28}O_4$ (344.4 amu)
(+)-Scabronine G
Methyl Ester
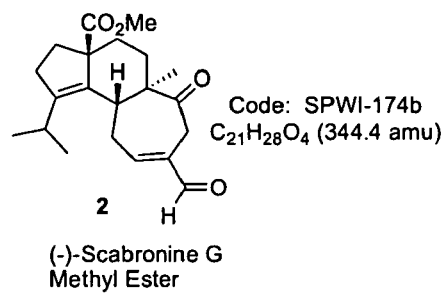
Code: SPWI-174b
$C_{21}H_{28}O_4$ (344.4 amu)
(−)-Scabronine G
Methyl Ester
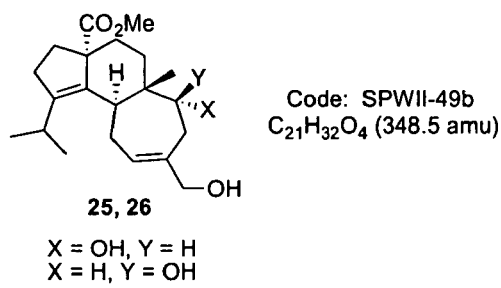
Code: SPWII-49b
$C_{21}H_{32}O_4$ (348.5 amu)
25, 26
X = OH, Y = H
X = H, Y = OH
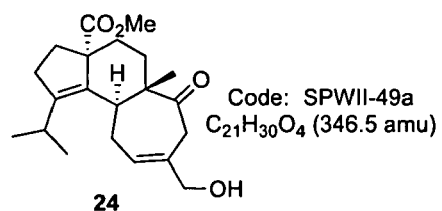
Code: SPWII-49a
$C_{21}H_{30}O_4$ (346.5 amu)
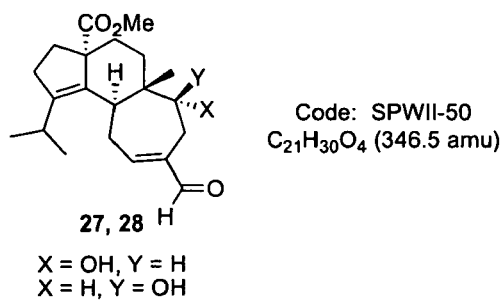
Code: SPWII-50
$C_{21}H_{30}O_4$ (346.5 amu)
27, 28
X = OH, Y = H
X = H, Y = OH

FIGURE 5B
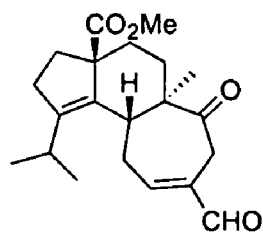
Scabronine G Methyl Ester
(Parent Compound)
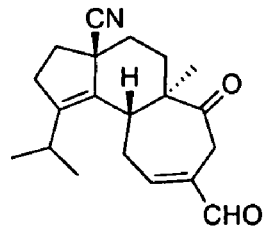
Scabronine Nitrile
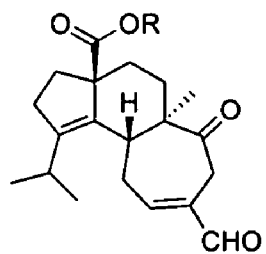
R = Ethyl, propyl, benzyl, etc.
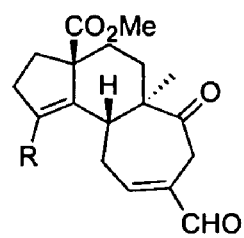
R = H, methyl, propyl, phenyl, etc.
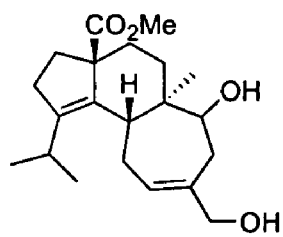
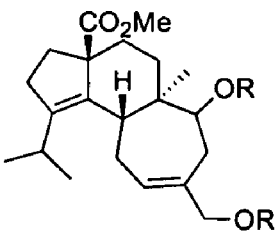
R = alkyl substituents

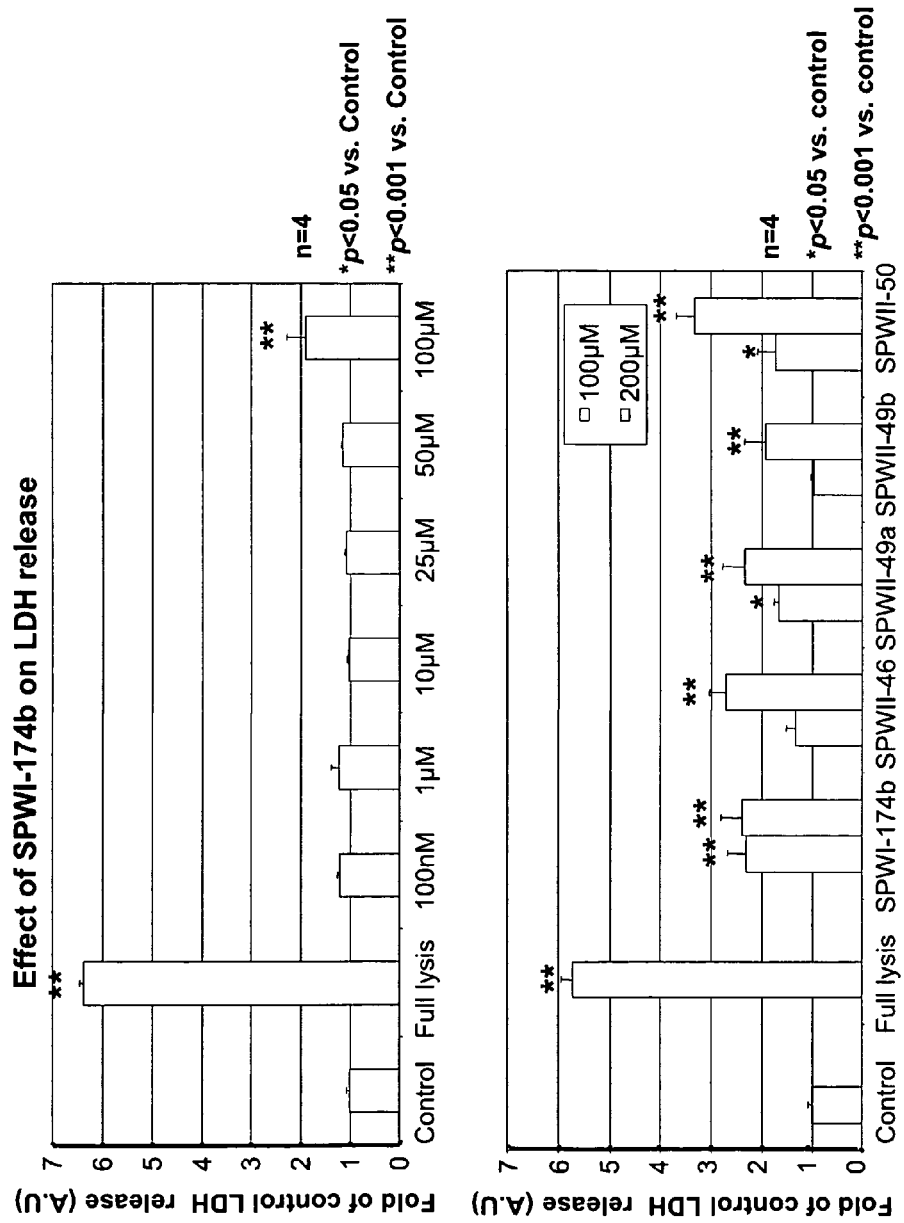

SYNTHESIS OF SCABRONINES AND ANALOGUES THEREOF

GOVERNMENT SUPPORT

The work described herein was supported, in part, by grants from the National Institutes of Health (Grant HL 25848). The United States government may have certain rights in the invention.

RELATED APPLICATIONS

The present application claims priority under 35 U.S.C. §119(e) to U.S. provisional patent application, U.S. Ser. No. 60/701,698, filed Jul. 22, 2005, which is incorporated herein by reference.

BACKGROUND OF THE INVENTION

The scabronines, metabolites from the bitter mushroom *Sarcodon scabrosus*, are related to a broader class of angularly fused tricyclic diterpenoids known as cyathanes (Kita et al. *Tetrahedron* 54:11877, 1998; incorporated herein by reference). The scabronines are distinct from other cyathanes by an angular C17 carboxyl group rather than a C17 methyl group. A report by Ohta disclosed that scabronine G induces the production and excretion of nerve growth factor (NGF) in human astroglial cells 1321N1 (Obara et al. *Mol. Pharmacol.* 59:1287, 2001; incorporated herein by reference). The methyl ester derivative of scabronine G is even more active in promoting excretion of NGF and an additional neurotrophin, interleukin 6 (IL-6). Consistent with these biochemical markers, dramatic neuronal differentiation of rat pheochromocytoma cells (PC-12) was observed. Accordingly, scabronine G and its methyl ester fall into a class of non-peptidyl structures exhibiting neurotrophic properties (Hefti et al. *Annu. Rev. Pharmacol. Toxicol.* 37:239, 1997; Luu et al. *Molecules* 5:1439, 2000; each of which is incorporated herein by reference).

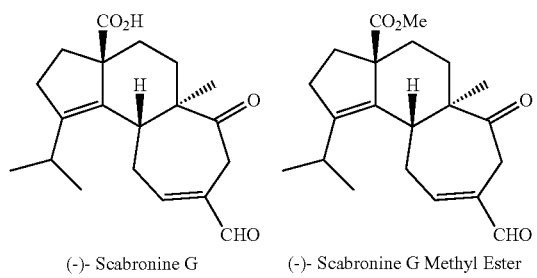

(-)- Scabronine G      (-)- Scabronine G Methyl Ester

Naturally occurring polypeptidyl neurotrophic factors play a central role in mediating neuronal growth and survival (Dawbarn et al *Neuropath. Appl. Neurobiol* 29:211, 2003; incorporated herein by reference). The study of the mechanism of action of these factors (cf. NGF and BDNF) is one of the central challenges in neuroscience. The clinical application of naturally occurring polypeptidyl neurotrophic factors in reversal of neurodegenerative disorders (cf. Parkinson's and Alzheimer's Diseases) has been investigated. However, unfavorable pharmacokinetics require their direct infusion into appropriate sectors of the brain, thus seriously complicating their progression to medical application (Kirik et al. *Nat. Neurosci.* 7:105, 2004; incorporated herein by reference).

One of the goals of research in this area is to identify promising small molecules with neurotrophic activity. In order to identify such small molecules, a total synthesis of scabronine G would be useful in preparing and identifying small molecules such as analogues of scabronine G with neurotrophic activity or other useful biological activities.

SUMMARY OF THE INVENTION

The present invention provides a novel synthesis of scabronine G and analogues thereof. The synthesis is particularly useful in preparing analogues of scabronine G, specifically analogues with different substituents at C-3, C-6, C-9, C-12, C-14, esters, and/or stereoisomers of scabronine G. In certain embodiments, the inventive compounds are meurotrophic agents useful in the treatment of neurodegenerative diseases. For examples, the compounds are useful in the treatment of Parkinson's Diseases, Alzheimer's Disease, and Huntington's Disease. These compounds may be used as pharmaceutical agents themselves or may be used as lead compounds in developing new pharmaceutical agents. Pharmaceutical compositions and methods of using these compounds to treat neurodegenerative diseases are also provided. The present invention also includes intermediates and synthetic methods useful in the preparation of scabronines and analogues thereof.

In one aspect of the invention, the compounds of the invention are of the formula:

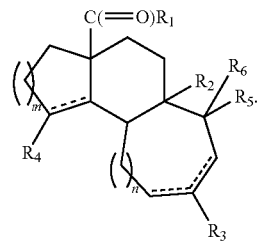

In certain particular embodiments, the stereochemistry is defined as shown in one of the formulae:

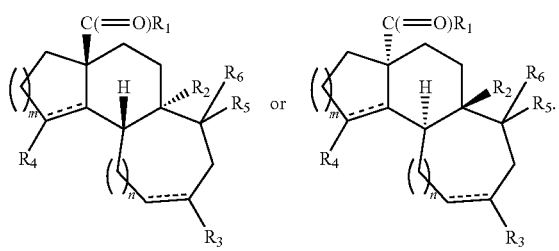

In certain embodiments, the compound is of one of the formulae:

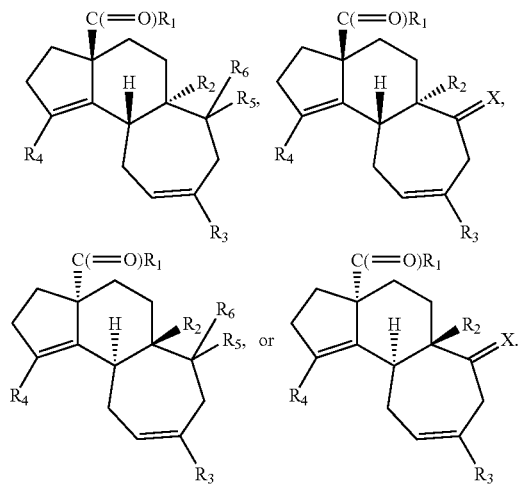

In certain embodiments, the inventive compounds have neutotrophic activity and are useful in treating neurodegenerative diseases such as Parkinson's disease, Alzheimer's disease, Huntington's disease, Pick's disease, etc. Without wishing to be bound by any particular theory, the compounds may act by inducing the production and excretion of neurotrophic agents such as nerve growth factor (NGF). In certain other embodiments, the inventive compounds have anti-proliferative activity and are useful in treating diseases such as cancer, autoimmune disease, neoplasms, diabetic retinopathy, etc. In certain embodiments, the compounds are cytotoxic. The analogues of scabronine G provided by the invention may be more potent and/or exhibit less side effects than natural products such scabronine G or other cyathanes.

The invention also provides pharmaceutical compositions of the inventive compounds for use in treating human diseases and veterinary diseases. The compounds of the invention are combined with a pharmaceutical excipient to form a pharmaceutical composition for administration to a subject. The pharmaceutical compositions of the inventive compounds may include immediate release formulations, extended release formulations, timed release formulations, etc. Methods of treating or preventing a neurodegenerative disease such as Alzheimer's Disease, Parkinson's Disease, or Huntington's Disease are also provided wherein a therapeutically effective amount of an inventive compound is administered to a subject. Methods of treating a proliferative disease such as cancer are also provided wherein a therapeutically effective amount of an inventive compound is administered to a subject.

In another aspect, synthetic methods and intermediates useful in preparing scabronine G or analogues thereof are provided. Such methods provide the ability to one of ordinary skill in this art to make various substitutions and variations as shown in the formulae herein. The individual steps in the synthesis of the inventive compounds are also considered to be within the invention.

Therefore, the novel synthesis of scabronine G provides methods for the preparation of new compounds which may be useful in treating neurodegenerative or proliferative diseases. The use of the compounds in pharmaceutical compositions and treatment regimens are also provided.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R— and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex mixtures of isomers.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomer or diastereomer. Alternatively, where the molecule contains a basic functional group, such as an amino group, or an acidic functional group, such as a carboxylic acid group, diastereomeric salts are formed with an appropriate optically-active acid or base, followed by resolution of the diastercomers thus formed by fractional crystallization or chromatographic means well known in the art, and subsequent recovery of the pure enantiomers.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-bcnzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl) ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkylp-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-

(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylpheriylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxylmethylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any pennissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of neurogenderative diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkoxy", or "thioalkyl" as used herein refers to an alkyl group, as previously defined, attached through an oxygen atom or through a sulfur atom. In certain embodiments, the alkyl, alkenyl, and alkynyl groups contain 1-20 alipahtic carbon atoms. In certain other embodiments, the alkyl, alkenyl, and alkynyl groups contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR', wherein R' is aliphatic, as defined herein. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$)$_2$; —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the structures that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the structures that are described herein.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the structures that are described herein.

The terms "halo" and "halogen" as used herein refer to an atom selected from fluorine, chlorine, bromine, and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolin idinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the structures which are described herein.

"Carbocycle": The term "carbocycle", as used herein, refers to an aromatic or non-aromatic ring in which each atom of the ring is a carbon atom.

"Independently selected": The term "independently selected" is used herein to indicate that the R groups can be identical or different.

"Labeled": As used herein, the term "labeled" means that a compound comprises at least one element, isotope, or chemical compound to enable the detection of the compound by any technique that would enable detection. Labels may be: a) isotopic labels, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; b) immune labels, which may be antibodies or antigens, which may be bound to enzymes (such as horseradish peroxidase) that produce detectable agents; or c) colored, luminescent, phosphorescent, or fluorescent dyes. It will be appreciated that the labels incorporated into the compound at any position that does not substantially interfere with the biological activity or characteristic of the compound that is being detected. In certain other embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

"Tautomers": As used herein, the term "tautomers" are particular isomers of a compound in which a hydrogen and double bond have changed position with respect to the other atoms of the molecule. Tautomers are interconnected through a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridione-hydroxypyridine forms.

Definitions of non-chemical terms used throughout the specification include:

"Animal": The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). A non-human animal may be a transgenic animal.

"Effective amount": In general, the "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient. For example, the effective amount of a compound with neurotrophic activity is the amount that results in a sufficient concentration in the brain to prevent the onset of the signs and symptoms of a neurodegenerative disease. In other embodiments, the effective amount reverses the signs and symptoms of a neurodegenerative disease. For example, the effective amount of a compound with anti-proliferative activity is the amount that results in a sufficient concentration at the site of the tumor to kill or inhibit the growth of tumor cells.

A "protein" or "peptide" comprises a polymer of amino acid residues linked together by peptide bonds. The term, as used herein, refers to proteins, polypeptides, and peptide of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

BRIEF DESCRIPTION OF THE DRAWING

FIGS. 5A and 5B show (+)-scabronine G, (-)-scabronine G, and various analogs of scabronine G.

FIG. 6 demonstrates the cytotoxicity of scabronine G and various analogs depicted in FIG. 5A toward mixed neuroglial cells.

DETAILED DESCRIPTION OF CERTAIN PREFERRED EMBODIMENTS OF THE INVENTION

Figure 1:
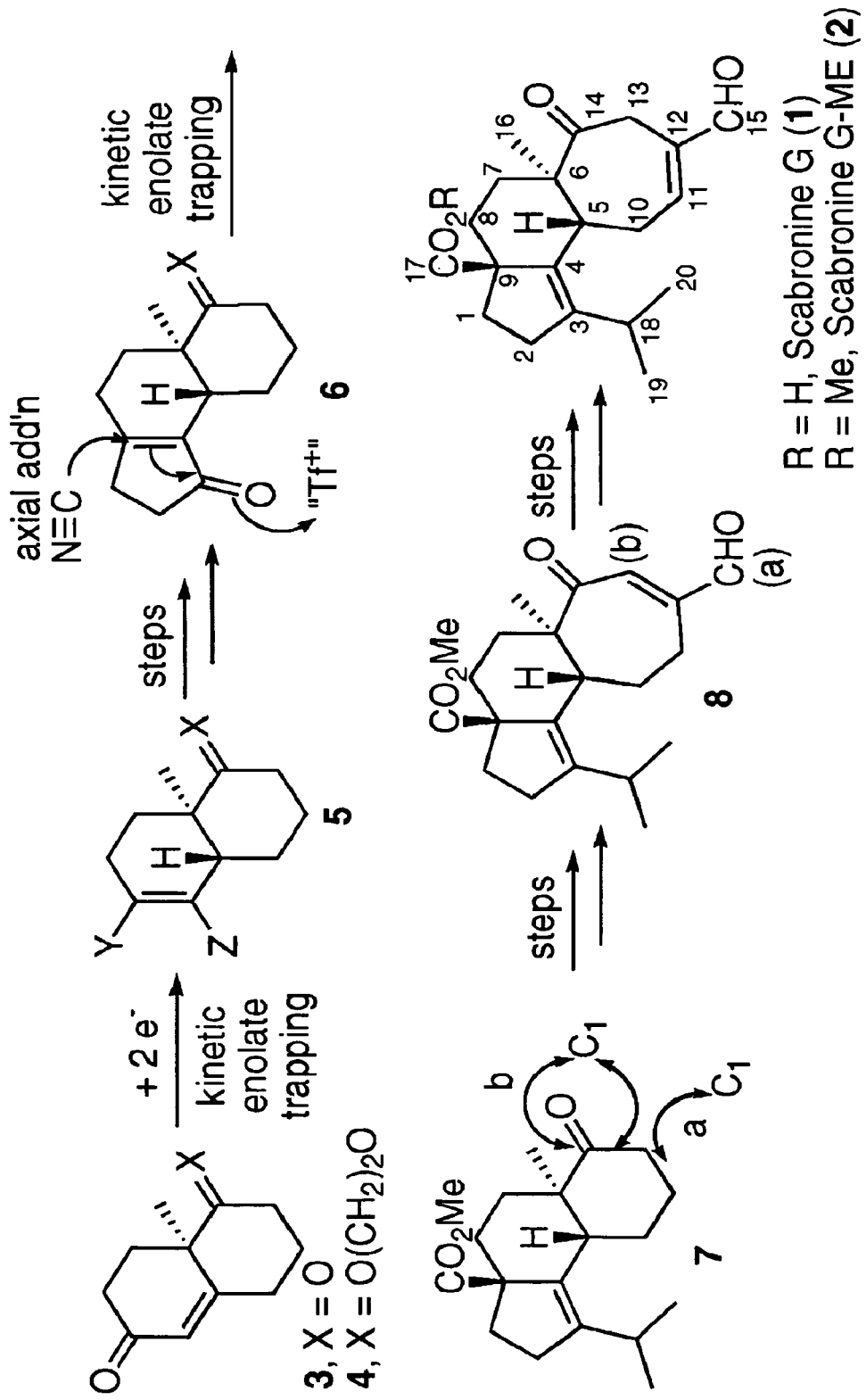
FIG. 1 shows a general synthetic strategy to scabronine G and analogs thereof.

The synthesis of scabronine G and analogues thereof is provided herein. Various compounds are accessible by this new synthetic route to scabronine G and are described herein. Certain compounds accessible by this novel route are neurotrophic agents useful in the treatment of neurodegenerative disorders. In other embodiments, the inventive compounds are cytotoxic and are useful in the treatment of proliferative diseases.

Compounds

In one aspect, the present invention provides compounds of the formula:

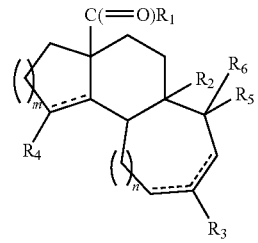

wherein each dashed line independently represents the absence of a bond or the presence of a carbon-carbon bond of a carbon-carbon double bond;

m is an integer between 0 and 3, inclusive;

n is an integer between 0 and 2, inclusive;

$R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; substituted or unsubstituted, branched or unbranched heteroaryl; —$OR_A$; —OH; —C(=O)$R_A$; —$CO_2R_A$; —CN; —SCN; —$SR_A$; —SH; —N($R_A$)$_2$; —NH$R_A$; —NH$_2$; or —C($R_A$)$_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_B$; —OH; —C(=O)$R_B$; —$CO_2R_B$; —CN; —SCN; —$SR_B$; —SH; —$SOR_B$; —$SO_2R_B$; —NO$_2$; —N($R_B$)$_2$; —NH$R_B$; —NH$_2$; —NHC(=O)$R_B$; —OC(=O)$R_B$; or —C($R_B$)$_3$; wherein each occurrence of $R_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —OH; —C(=O)$R_C$; —$CO_2R_C$; —CN; —SCN; —$SR_C$; —SH; —$SOR_C$; —$SO_2R_C$; —$NO_2$; —$N(R_C)_2$; —$NHR_C$; —$NH_2$; —NHC(=O)$R_C$; —OC(=O)$R_C$; or —C($R_C$)$_3$; wherein each occurrence of $R_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —OH; —C(=O)$R_D$; —$CO_2R_D$; —CN; —SCN; —$SR_D$; —SH; —$SOR_D$; —$SO_2R_D$; —$NO_2$; —$N(R_D)_2$; —$NHR_D$; —$NH_2$; —NHC(=O)$R_D$; —OC(=O)$R_D$; or —C($R_D$)$_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_E$; —OH; —C(=O)$R_E$; —$CO_2R_E$; —CN; —SCN; —$SR_E$; —SH; —$SOR_E$; —$SO_2R_E$; —$NO_2$; —$N(R_E)_2$; —$NHR_E$; —$NH_2$; —NHC(=O)$R_E$; —OC(=O)$R_E$; or —C($R_E$)$_3$; wherein each occurrence of $R_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_F$; —OH; —C(=O)$R_F$; —$CO_2R_F$; —CN; —SCN; —$SR_F$; —SH; —$SOR_F$; —$SO_2R_F$; —$NO_2$; —$N(R_F)_2$; —$NHR_F$; —$NH_2$; —NHC(=O)$R_F$; —OC(=O)$R_F$; or —C($R_F$)$_3$; wherein each occurrence of $R_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_5$ and $R_6$ may be take together to form =O, =S, =$NR_E$, =C($R_E$)$_2$, or a carbocyclic or heterocyclic moiety; or a therapeutically acceptable salt thereof.

In certain embodiments, the ester functionality at C-9 is replaced with a nitrile moiety, and the resulting compounds are of the formula:

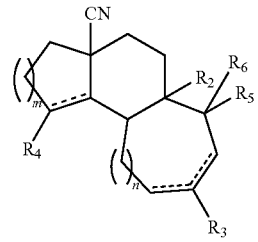

wherein $R_2$, $R_3$, $R_4$, $R_5$, $R_6$, and the dashed lines are as defined herein.

In certain embodiments, at least two of the dashed lines in the structures above represent carbon-carbon bonds. In certain embodiments, only one of the dashed lines in the structures above represents a carbon-carbon bond. In certain embodiments, the resulting double bonds are in the cis configuration. In other embodiments, all the dashed lines represent the absence of a bond. Exemplary structures include compounds of the formulae:

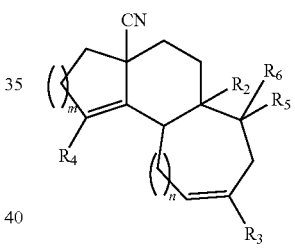 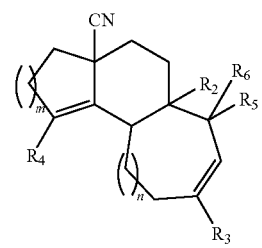

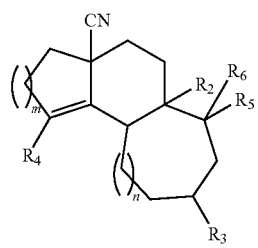 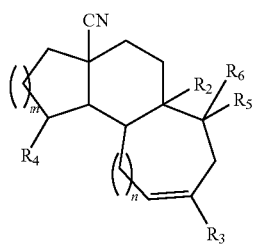

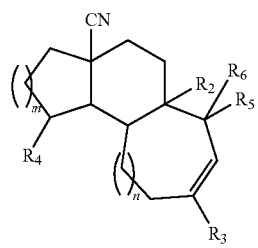 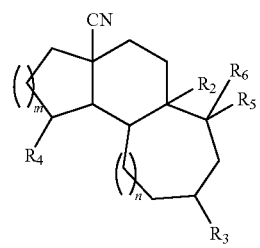

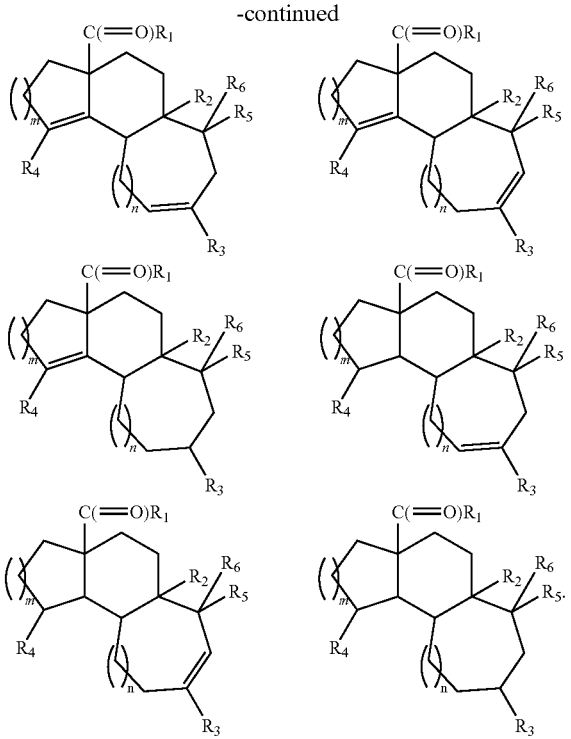

In certain embodiments, m is 1. In other embodiments, m is 2.

In certain embodiments, n is 1. In other embodiments, n is 0.

In certain embodiments, m and n are both 1.

In certain embodiments, $R_1$ is hydrogen. In certain embodiments, $R_1$ is —$OR_A$. In certain particular embodiments, $R_1$ is —$OR_A$, wherein $R_A$ is $C_1$-$C_6$alkyl. In certain particular embodiments, $R_1$ is —OMe, —OEt, or —OPr. In certain embodiments, $R_1$ is —OMe. In certain embodiments, $R_1$ is —OH. In other embodiments, $R_1$ is —$N(R_A)_2$. In certain embodiments, $R_1$ is —$NHR_A$. In other embodiments, $R_1$ is —$NH_2$. In certain embodiments, $R_1$ is $C_1$-$C_6$ aliphatic. In certain embodiments, $R_1$ is $C_1$-$C_6$ alkyl. In certain embodiments, $R_1$ is halogen.

In certain embodiments, $R_2$ is hydrogen. In certain embodiments, $R_2$ is $C_1$-$C_6$ aliphatic. In certain particular embodiments, $R_2$ is $C_1$-$C_6$ alkyl. In particular embodiments, $R_2$ is methyl. In other embodiments, $R_2$ is ethyl. In yet other embodiments, $R_2$ is propyl. In certain embodiments, $R_2$ is a halogenated $C_1$-$C_6$ aliphatic moiety (e.g., —$CF_3$, —$CHF_2$, —$CH_2F$).

In certain embodiments, $R_3$ is hydrogen. In other embodiments, $R_3$ is $C_1$-$C_6$ aliphatic. In yet other embodiments, $R_3$ is $C_1$-$C_6$ alkyl. In certain embodiments, $R_3$ is methyl, ethyl, or propyl. In certain embodiments, $R_3$ is acyl. In certain embodiments, $R_3$ is —CHO. In other embodiments, $R_3$ is —$COR_C$, —$CO_2R_C$, or —$CON(R_C)_2$. In certain embodiments, $R_3$ is hydroxymethyl (—$CH_2OH$). In certain embodiments, $R_3$ is —$CH_2OR_C$. In certain embodiments, $R_3$ is —$CH_2OR_C$, wherein $R_C$ is $C_1$-$C_6$ alkyl. In certain embodiments, $R_3$ is —$CH_2OR_C$, wherein $R_C$ is substituted or unsubstituted aryl or heteroaryl.

In certain embodiments, $R_4$ is hydrogen. In other embodiments, $R_4$ is $C_1$-$C_{12}$ aliphatic. In yet other embodiments, $R_4$ is $C_1$-$C_6$ aliphatic. In certain embodiments, $R_4$ is $C_1$-$C_6$ alkyl. In certain embodiments, $R_4$ is methyl. In other embodiments, $R_4$ is ethyl. In yet other embodiments, $R_4$ is propyl. In certain embodiments, $R_4$ is iso-propyl. In certain embodiments, $R_4$ is butyl. In certain embodiments, $R_4$ is iso-butyl. In other embodiments, $R_4$ is tert-butyl. In other embodiments, $R_4$ is pentyl. In yet other embodiments, $R_4$ is hexyl.

In certain embodiments, $R_5$ is hydrogen. In other embodiments, $R_5$ is —OH. In yet other embodiments, $R_5$ is —$OR_E$. In certain embodiments, $R_5$ is $C_1$-$C_6$ aliphatic. In other embodiments, $R_5$ is methyl, ethyl, or propyl.

In certain embodiments, $R_6$ is hydrogen. In other embodiments, $R_6$ is —OH. In yet other embodiments, $R_6$ is —$OR_F$. In certain embodiments, $R_6$ is $C_1$-$C_6$ aliphatic. In other embodiments, $R_6$ is methyl, ethyl, or propyl.

In certain embodiments, $R_5$ is —OH, and $R_6$ is hydrogen. In other embodiments, $R_5$ is hydrogen, and $R_6$ is —OH. In certain embodiments, $R_5$ is —$OR_E$, and $R_6$ is hydrogen. In other embodiments, $R_5$ is hydrogen, and $R_6$ is —$OR_F$. In certain embodiments, both $R_5$ and $R_6$ are hydrogen. In certain embodiments, $R_5$ and $R_6$ taken together form a cyclic structure. In certain embodiments, $R_5$ and $R_6$ taken together form a cyclic acetal moiety. In certain embodiments, $R_5$ and R6 taken together are =O. In certain embodiments, $R_5$ and $R_6$ taken together are =S. In other embodiments, $R_5$ and $R_6$ taken together are =$NR_E$. In other embodiments, $R_5$ and $R_6$ taken together are =$C(R_E)_2$.

In certain embodiments, the stereochemistry of the core tricylic ring system is defined as shown in the formula:

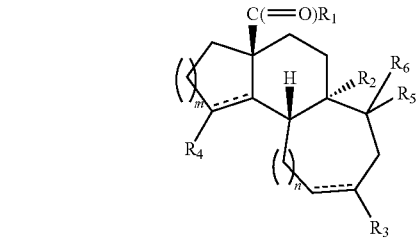

wherein the dashed line, m, n, $R_1$, $R_2$, $R_3$, $R_4$, $R_5$, and $R_6$ are as defined in the genera, classes, subclasses, and species described herein.

In other embodiments, the stereochemistry of the core tricylic ring system is defined as shown in the formula:

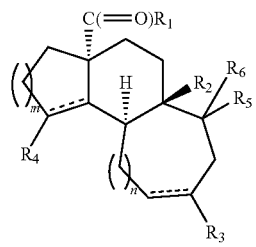

wherein the dashed line, m, n, $R_1$, $R_2$, $R_3$, $R_4$, $R_5$, and $R_6$ are as defined in the genera, classes, subclasses, and species described herein.

In certain embodiments, the compound is of the formula:

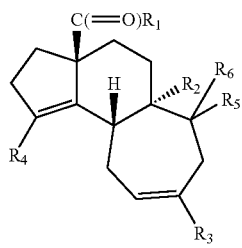

wherein
both dashed lines represent bonds; and
$R_1$, $R_2$, $R_3$, $R_4$, $R_5$, and $R_6$ are as defined in the genera, classes, subclasses, and species described herein.

In certain embodiments, the compound is of the formula:

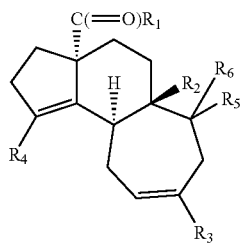

wherein
both dashed lines represent bonds; and
$R_1$, $R_2$, $R_3$, $R_4$, $R_5$, and $R_6$ are as defined in the genera, classes, subclasses, and species described herein. In certain embodiments, one of $R_5$ and $R_6$ is —OH, and the other is hydrogen. In certain embodiments, one of $R_5$ and $R_6$ is —OH, and the other is $C_1$-$C_6$ alkyl (e.g., methyl). In certain embodiments, $R_5$ and $R_6$ together form a cyclic acetal. In certain embodiment, $R_1$ is —OH or —OMe, $R_2$ is methyl, and $R_4$ is iso-propyl. In certain embodiments, $R_1$ is —OMe. In certain embodiments, $R_3$ is —CH$_2$OH. In other embodiments, $R_3$ is —CHO.

In certain embodiments, $R_5$ and $R_6$ are taken together. In certain embodiments, the compound is of the formula:

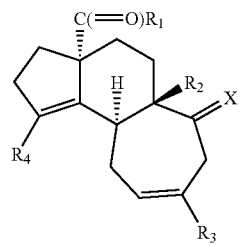

wherein
X is O, S, NH, NR$_E$, or C(R$_E$)$_2$; and
$R_1$, $R_2$, $R_3$, $R_4$, and R$_E$ are as defined in the genera, classes, subclasses, and species described herein. In certain embodiments, the compound is of the formula:

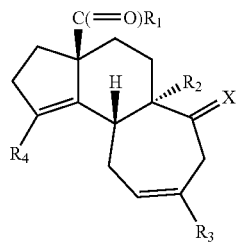

wherein
X is O, S, NH, NR$_E$, or C(R$_E$)$_2$; and
$R_1$, $R_2$, $R_3$, $R_4$, and R$_E$ are as defined in the genera, classes, subclasses, and species described herein. In certain embodiment, X is O, $R_1$ is —OH or —OMe, $R_2$ is methyl, and $R_4$ is iso-propyl. In certain embodiments, $R_1$ is —OMe. In certain embodiments, $R_3$ is —CH$_2$OH. In other embodiments, $R_3$ is —CHO.

Exemplary compounds of the invention include:

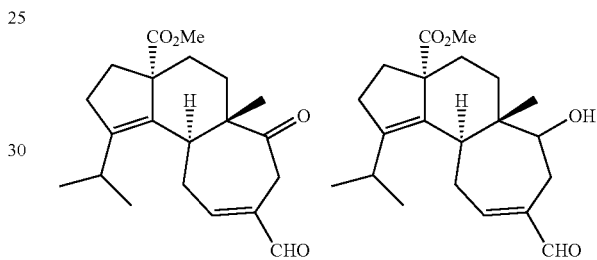

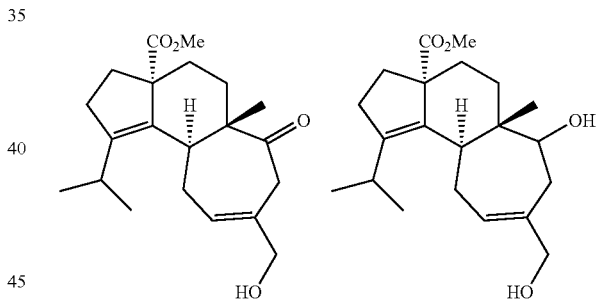

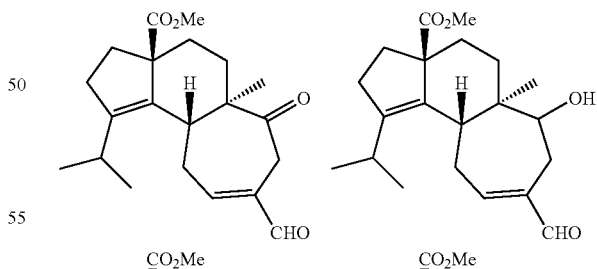

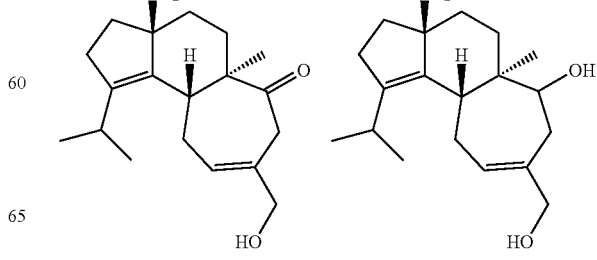

-continued

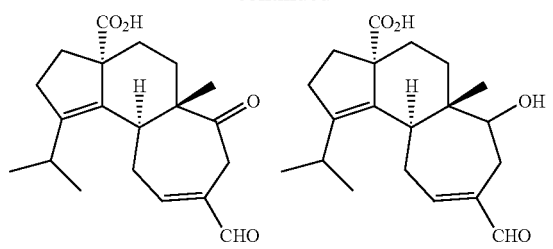

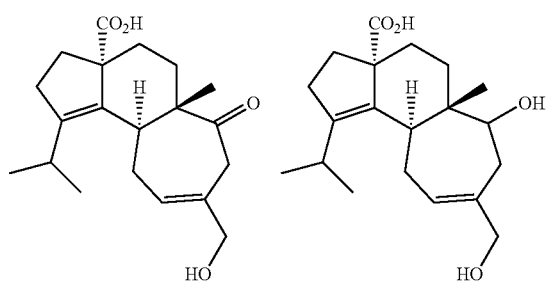

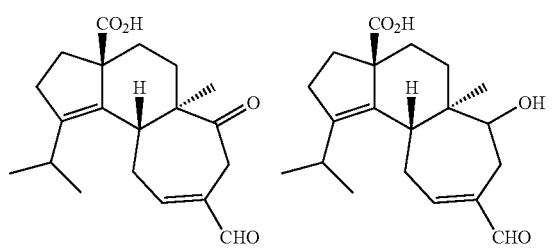

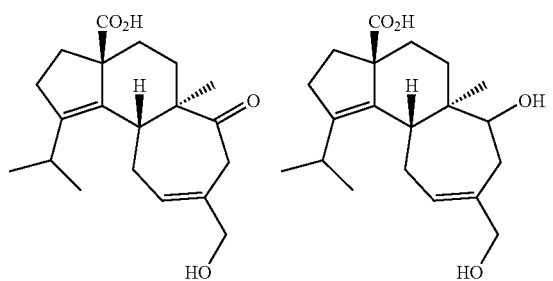

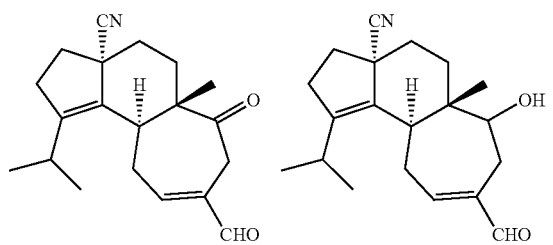

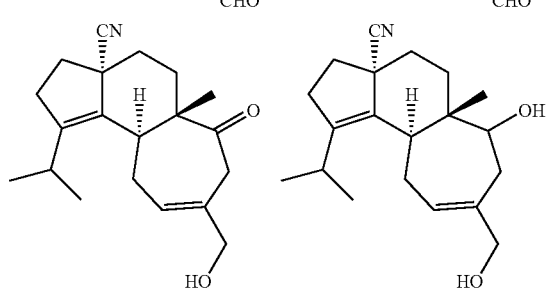

-continued

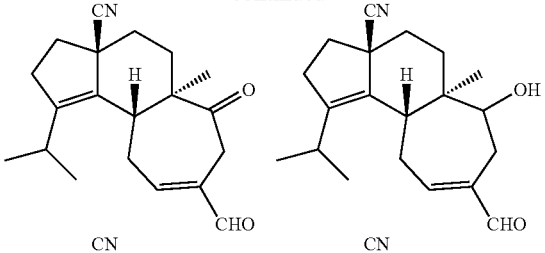

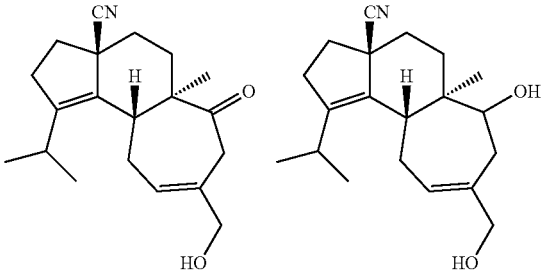

As will be appreciated by one of skill in this art, compounds of invention include derivatives, labeled forms, salts, pro-drugs, isomers, and tautomers thereof. Derivatives include protected forms. Salts include any pharmaceutically acceptable salts including HCl, HBr, HI, acetate, sulfonate (e.g., besylate, p-toluenesulfonate, mesylate, etc.) and fatty acid (e.g., lactate, citrate, myristoleate, oleate, valerate) salts.

The compounds are useful a pharmaceutical agents in the treatment of human or veterinary disease such as neurodegenerative diseases or proliferative diseases. In certain embodiments, the compounds are useful intermediates in the synthesis of pharmaceutical reagents. In certain embodiments, the compounds are useful research tools. For example, the compounds are useful in studying the release or action of neurotrophic agents.

As will be appreciated by one of skill in this art, the invention includes compositions in which the compounds are at least 90%, 95%, 98%, 99%, or 99.9% pure.

Methods of Synthesis

A novel synthesic strategy toward scabronine G is shown in FIG. 1. An exemplary synthesis of scabronine G and its methyl ester is shown in more detail in FIGS. 2 and 3 and is described in Example 1 below. As will be appreciated by one of skill in this art, various modifications can be made to the starting materials and reagents used in the synthesis to provide the compounds of the invention and useful intermediates.

Figure 2:
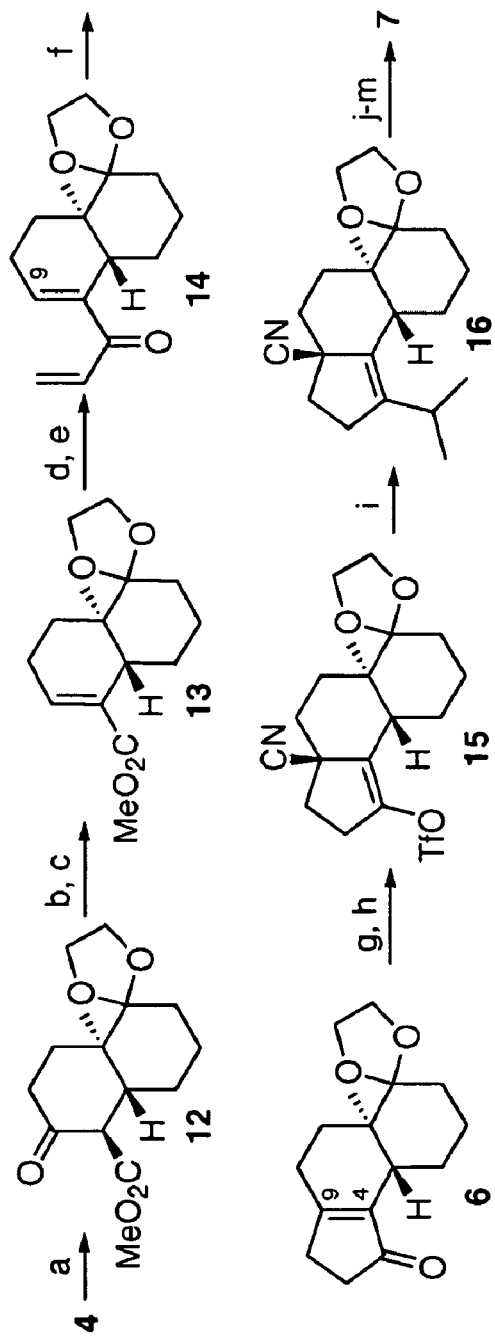
FIG. 2 shows a synthesis of intermediate 7 as shown in FIG. 1.

The synthesis of scabronine G begins with protection of the Wieland-Miescher ketone (3) to form 4 (FIGS. 1 and 2). As would be appreciated by one of skill in this art, various analogs of the starting ketone may be used in the synthesis. In particular, the angular methyl group may be replaced with other aliphatic or heteroaliphatic moieties. Reduction and acylation of 4 with Mander's reagent afforded the known ketoester 12. Conversion of the ketone to its enol triflate followed by hydride reduction gave unsaturated ester 13. The ester was subsequently converted to the corresponding Weinreb amide, which was subsequently reacted with vinylmagnesium bromide or other vinyl anion to yield the divinyl ketone, 14. Lewis acid-mediated Nazarov cyclization provided the requisite cyclopentenone 6 as a single olefin isomer. Conjugate addition of Nagata's reagent to the enone 6 followed by trapping of the resulting enolate with a silyl-protecting agent (e.g., TMSCl) gave the silyl enol ether. The silyl enol ether was then converted to compound 15. The isopropyl group or other alkyl group is then installed via a coupling reaction (e.g., a Negishi coupling reaction) to yield nitrile 16. The nitrile is then converted to the corresponding ester (e.g., methyl ester) and deketalization provided the cyclohexanone 7.

Ketone 7 is then converted to the thiopropylmethylidene intermediate 17. Addition of lithiated methoxymethyl phenyl sulfide afforded diasteromeric alcohols 18. Treatment of 18 with HgCl$_2$ in acidic medium afforded the ring expanded cross-conjugated cycloheptenone 8. Thermodynamically favored isomerization of the olefin in 8 afforded scabronine G methyl ester. The methyl ester is then optionally hydrolyzed (e.g., with base) to form scabronine G.

As will be appreciated by one of skill in this art, the aldehyde moiety at C12 may be reduced, oxidized, protected, or otherwise modified. In addition, the angular methyl ester at C9 may also be hydrolysed, reduced, oxidized, or otherwise modified. For example, a longer alkyl group may replace the methyl group. The angular methyl group at C6 may be altered by starting the synthesis with the corresponding starting material. Any of the double bonds of scabronine G may be reduced, oxidized, or isomerized. Any of these modifications to the exemplary synthesis of scabronine G as detailed herein may be modified to prepare the compounds of the invention. In certain embodiments, these modifications are combined to prepare an inventive compound.

In certain embodiments, the synthesis of scabronine G or analogues thereof staring from a readily available pyrroglutamate derivatve include the following steps:

(a) providing a ketone of formula:

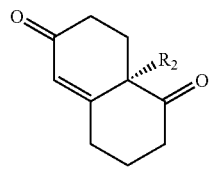

wherein R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —OH; —C(=O)R$_B$; —CO$_2$R$_B$; —CN; —SCN; —SR$_B$; —SH; —SOR$_B$; —SO$_2$R$_B$; —NO$_2$; —N(R$_B$)$_2$; —NHR$_B$; —NH$_2$; —NHC(=O)R$_B$; —OC(=O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; preferably, C$_1$-C$_6$ alkyl (e.g., methyl);

(b) protecting the ketone to form a protected ketone of formula:

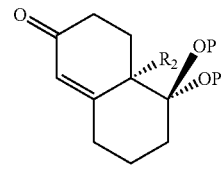

wherein each occurrence of P is an oxygen protecting group (e.g., a cyclic acetal);

(c) reducing the protected ketone to form the methyl ester of formula:

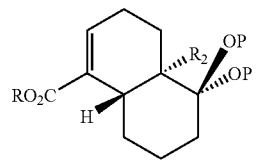

wherein R is C$_1$-C$_6$ alkyl;

(d) adding a vinyl moiety to the ester to form the divinyl ketone of the formula:

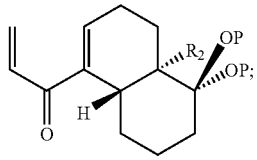

(e) cyclizing the divinyl ketone under suitable condition to form the five-membered ring-containing tricyclic compound of formula:

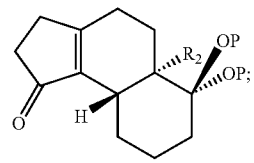

(f) addition of a nitrile moiety to the unsaturated ketone and trapping of the enolate to form a compound of formula:

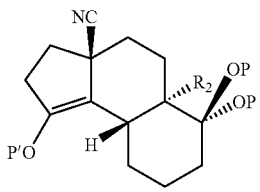

wherein P' is an oxygen protecting group (e.g., a silyl protecting group, Tf, Ms);

(g) coupling of the $R_4$ moiety to form a compound of formula:

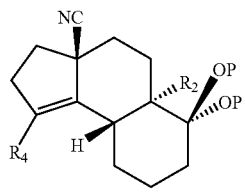

wherein $R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —OH; —C(=O)$R_D$; —$CO_2R_D$; —CN; —SCN; —$SR_D$; —SH; —$SOR_D$; —$SO_2R_D$; —$NO_2$; —$N(R_D)_2$; —$NHR_D$; —$NH_2$; —NHC(=O)$R_D$; —OC(=O)$R_D$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; preferably, $C_1$-$C_6$ alkyl (e.g., methyl, ethyl, iso-propyl, etc.), aryl (e.g., phenyl), or heteroaryl;

(h) converting the nitrile to an acyl moiety (e.g., ester);

(i) deprotecting the ketone (e.g., by deketalization) to yield a cyclohexanone of formula:

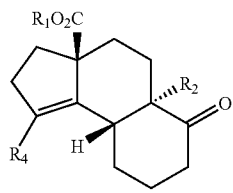

wherein $R_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; substituted or unsubstituted, branched or unbranched heteroaryl; —$OR_A$; —OH; —C(=O)$R_A$; —$CO_2R_A$; —CN; —SCN; —$SR_A$; —SH; —$N(R_A)_2$; —$NHR_A$; —$NH_2$; or —$C(R_A)_3$; wherein each occurrence of $R_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; preferably, $R_1$ is $C_1$-$C_6$ alkyl (e.g., methyl);

(j) addition of thiopropylmethylidene to form a compound of formula:

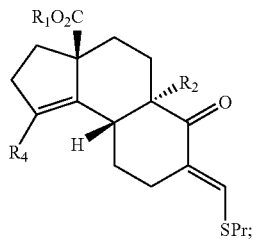

(k) ring expansion of the cyclohexanone ring to form a cycloheptenone of formula:

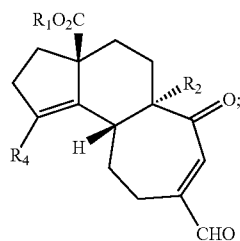

(l) isomerizing the double bond under suitable conditions to form a compound of formula:

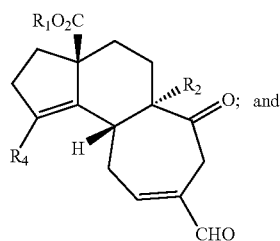

(m) optionally, hydrolyzing the ester to form the carboxylic acid of formula:

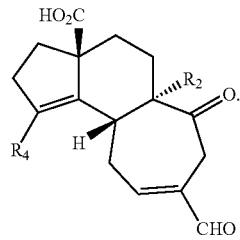

In certain embodiments, $R_1$, $R_2$, and $R_4$ are defined as described herein. In certain embodiments, $R_1$ is methyl. In other embodiments, $R_4$ is so-propyl. In other embodiments, $R_2$ is methyl.

In certain embodiments, the aldehyde moiety of:

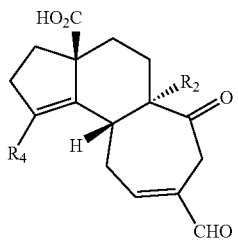

is reduced to yield an alcohol of formula:

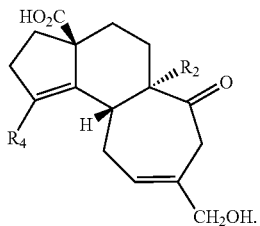

The resulting alcohol may then be optionally protected or alkylated.

In other embodiments, any of the double bonds of:

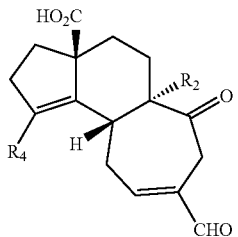

are reduced or oxidized.

Pharmaceutical Compositions

This invention also provides a pharmaceutical preparation comprising at least one of the compounds as described above and herein, or a pharmaceutically acceptable derivative thereof. In certain embodiments, the compound induces the release of neurotrophic agents. In other embodiments, the compound induces the growth or division of neuronal cells. In certain embodiments, the compounds induces neurite formation. In other embodiments, the compound inhibits the growth of or kills cells, particular tumor cells. In other embodiments, the compounds show cytostatic or cytotoxic activity against neoplastic cells such as cancer cells. In yet other embodiments, the compounds inhibit the growth of or kill rapidly dividing cells such as stimulated inflammatory cells.

The present invention provides novel compounds having neurotrophic activity, and thus the inventive compounds are useful for the treatment of a variety of medical conditions including neurodegenerative disease and psychiatric diseases. Exemplary neurodegenerative diseases include Alexander disease, Alper's disease, amyotrophic lateral sclerosis, ataxia telangiectasia, Batten disease (Spielmeyer-Vogt-Sjogren-Batten disease), Canavan disease, Cockayne syndrome, corticobasal degeneration, Creutzfeld-Jakob's disease, Huntington's disease, Kennedy's disease, Krabbe disease, Lewy body disease, Machado-Joseph disease (spinocerebellar ataxia type 3), multiple sclerosis, multiple system atrophy, Pelizaeus-Merzbacher disease, primary lateral sclerosis, Refsum's disease, Sandoff disease, Schilder's disease, spinocerebellar ataxia, spinal muscular atrophy, Steele-Richardson-Olszewski disease, dementia, Alzheimer's disease, Parkinson's disease, Pick's disease, senility, Lewy body diseases, synucleinopathies, stroke, tabes dorsalis, etc. The compounds are particularly useful in treating diseases associated with the deterioration of neurons. The administration of the inventive compounds prevents or restores brain function. In certain embodiments, the administration of the inventive compounds improves movement. In other embodiments, the administration improves cognitive function such as memory.

The present invention provides novel compounds having antimicrobial and/or antiproliferative activity, and thus the inventive compounds are useful for the treatment of a variety of medical conditions including infectious diseases, cancer, autoimmune diseases, inflammatory diseases, and diabetic retinopathy. Accordingly, in another aspect of the present invention, pharmaceutical compositions are provided, wherein these compositions comprise any one of the compounds as described herein, and optionally comprise a pharmaceutically acceptable carrier.

In certain embodiments, these compositions optionally further comprise one or more additional therapeutic agents. In other embodiments, these compositions further comprise an anti-inflammatory agent such as aspirin, ibuprofen, acetaminophen, etc., pain reliever, or anti-pyretic. In other embodiments, these compositions further comprise acetylcholinesterase inhibitors, neurotransmitter agonists, neurotransmitter antagonists, neurotropic agents, an anti-emetic agent, a pain reliever, a multi-vitamin, etc.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1-19, 1977; incorporated herein by reference. The salts can be prepared in situ during the final isolation and purification of the compounds of the invention, or separately by reacting the free base functionality with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. In certain embodiments, the esters are cleaved by enzymes such as esterases.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicles, dispersion or suspension aids, surface active agents, isotonic agents, thickening or emulsifying agents, preservatives, solid binders, lubricants and the like, as suited to the particular dosage form desired. Remington's *Pharmaceutical Sciences*, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-cancer compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; Cremophor; Solutol; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

The invention further provides a method of treating or preventing neurodegenerative diseases. The invention also provides a method of treating cancer and/or inhibiting tumor growth. The method involves the administration of a therapeutically effective amount of the compound or a pharmaceutically acceptable derivative thereof to a subject (including, but not limited to a human or animal) in need of it.

The compounds and pharmaceutical compositions of the present invention may be used in treating or preventing any disease or conditions including proliferative diseases (e.g., cancer, benign neoplasms, diabetic retinopathy), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound of pharmaceutical compositions to the animal. In certain embodiments, the compound or pharmaceutical composition is administered orally. In other embodiments, the compound or pharmaceutical composition is administered parenterally.

The exact amount required will vary from subject to subject, depending on the species, age, and general condition of the subject, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such an Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

These and other aspects of the present invention will be further appreciated upon consideration of the following Examples, which are intended to illustrate certain particular embodiments of the invention but are not intended to limit its scope, as defined by the claims.

EXAMPLES

Example 1

Total Synthesis of (−)-Scabronine G, an Inducer of Neurotrophic Factor Production The scabronines, metabolites from the bitter mushroom *Sarcodon scabrosus*, are related to a broader class of angularly fused tricyclic diterpenoids known as cyathanes (The scabronines are distinct from all other cyathanes by an angular C17 carboxyl group rather than C17 methyl: Kita et al. *Tetrahedron* 1998, 54, 11877; which is incorporated herein by reference). Our interest in scabronine G (1) followed a report by Ohta which disclosed it to induce the production and excretion of nerve growth factor (NGF) in 1321N1 human astroglial cells (Obara et al. *Mol. Pharmacol.* 2001, 59, 1287; incorporated herein by reference). Its methyl ester derivative (2) is even more active in promoting excretion of NGF and an additional neurotrophin, interleukin 6 (IL-6). Consistent with these biochemical markers, dramatic neuronal differentiation of rat pheochromocytoma cells (PC-12) was also observed. Accordingly, compounds 1 and 2 fall in to a class of non-peptidyl structures exhibiting neurotrophic properties (Hefti, F. *Annu. Rev. Pharmacol. Toxicol.* 1997, 37, 239; Luu et al. *Molecules* 2000, 5, 1439; each of which is incorporated herein by reference).

Naturally occurring polypeptidyl neurotrophic factors play a central role in mediating neuronal growth and survival (Dawbarn et al. *Neuropath. Appl. Neurobiol.* 2003, 29, 211; incorporated herein by reference). The study of the mechanism of action of these factors (cf. NGF and BDNF) is one of the central challenges to the neurosciences. The clinical application of naturally occurring polypeptidyl neurotrophic factors in reversal of neurodegenerative disorders (cf. Parkinson's, Alzheimer's Diseases) has been investigated. However, unfavorable pharmacokinetics require their direct infusion into appropriate sectors of the brain, thus seriously complicating their progression to medical application (Kirik et al. *Nat. Neurosci.* 2004, 7, 105; incorporated herein by reference).

One of the goals of our laboratory is that of identifying promising small molecules with neurotrophic activity. Toward this end, we are drawn to natural products which exhibit such activity and whose structures invite new possibilities in chemical synthesis. Earlier in our program we reported total syntheses of the extensively oxidized neurotrophic agents tricycloillicinone, merrilactone A, and jiadefenin (Pettus et al. *J. Am. Chem. Soc.* 2000, 122, 6160; Birman et al. *J. Am. Chem. Soc.* 2002, 124, 2080; Cho et al. *J. Am. Chem. Soc.* 2004, 126, 14358; each of which is incorporated herein by reference). The scabronines struck us even more important in light of the data reported above. Herein we describe the first total synthesis of scabronine G (for recent syntheses of related cyathanes, see: Snider, B. B.; Vo, N. H.; O'Neil, S. V.; Foxman, B. M. *J. Am. Chem. Soc.* 1998,118, 7644; Piers, E.; Gilbert, M.; Cook, K. L. *Org. Lett.* 2000, 2, 1407; Takano, M.; Umino, A.; Nakada, M. *Org. Lett.* 2004, 6, 4897; Trost, B. M.; Dong, L.; Schroeder, G. M. *J. Am. Chem. Soc.* 2005, 127, 2844; each of which is incorporated herein by reference).

We operated from the pleasingly simple idea that scabronine G can be viewed as an annulated (ring A) one-carbon ring-expanded (ring C) version of the (−)-Wieland-Miescher ketone (3) (Application of 3 to reach non-steroidal terpenoids arose in the synthesis of longifolene: Corey et al. *J. Am. Chem. Soc.* 1961, 83, 1251; incorporated herein by reference. For the synthesis of 3, see: Buchschacher, P.; First, A.; Gutzwiller, *J. Org. Syn., Coll. Vol. VII* 1990, 368; incorporated herein by reference). Trapping of the reductively generated trans BC fused kinetic enolate derived from 4 would provide the as yet undefined 5 (FIG. 1). The condition placed on the Y and Z functions of 5 is that they be integratable to afford 6. Anticipating conjugate attack of a cyano nucleophile on the 4,9 enone (Nagata et al. *J. Am. Chem. Soc.* 1972, 94, 4644; incorporated herein by reference), the remote C6-C9 backbone relationship would be solved through sound stereoelectronic principles rather than through ad hoc steric hindrance based selectivities. In the concluding phases, sequential interpolation of two $C_1$ fragments, which emerge as C15 and C13, respectively, would lead to 8 and thence to 1 and 2.

We first describe an initiative which, while unsuccessful from the perspective of our proposed total synthesis, provided a valuable teaching in structuring our later work. From 4 (Ciceri et al. *Tetrahedron Lett.* 1997, 38, 389; incorporated herein by reference), kinetically controlled enol triflation (McMurry et al. *Tetrahedron Lett*, 1983, 24, 979; incorporated herein by reference) followed by Stille cross-coupling gave diene 9 in the expected stereo- and regio-controlled manner (Scheme 1). Chemoselective hydroboration of the terminal olefin and further oxidation provided carboxylic acid 10. Interestingly, acid-mediated Friedel-Crafts type annulation of 10 provided 11 rather than the expected 6.

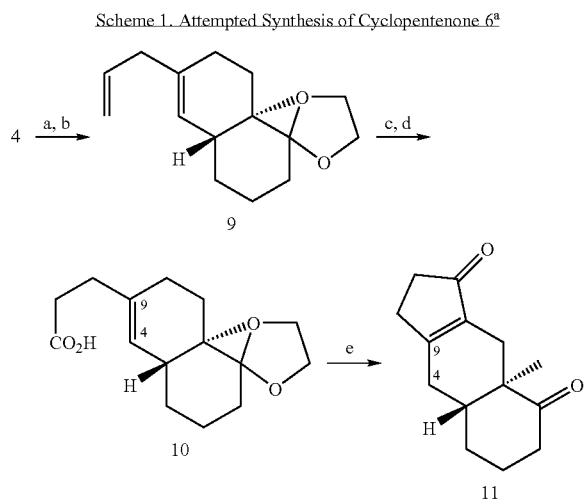

[a]Key: (a) Li/NH$_3$, PhNTf$_2$, THF, -78° C., 73%; (b) allylSn(Bu)$_3$, Pd(PPh$_3$)$_4$, LiCl, THF, 55° C., 96%; (c) 9-BBN, THF; NaOH, H$_2$O$_2$, 0° C., 92%; (d) Jones reagent, acetone, 82%; (e) PPA, CH$_2$Cl$_2$, 75° C., 60%

We took this then disappointing outcome to presage potential problems in fashioning the cyclopentenone moiety of 6 by cyclization of a three carbon fragment based at C9 (see 5). Such a modality would require an attack at C4 which is 1,3-diaxial to the angular methyl group and ortho to the hindered C ring. The take-home lesson for us, still keeping within the spirit of FIG. 1, was to securely install the substitution at C4 via the Z group, leaving the cyclization event to occur at C9. Reduction of 4 and acylation with Mander's reagent afforded the known ketoester 12 (FIG. 2) (Ling et al. *J. Org. Chem.* 2001, 66, 8843; incorporated herein by reference. For seminal work on reductive carboxylations of this type, see: Stork et al. *J. Am. Chem. Soc.* 1965, 87, 275; incorporated herein by reference). Conversion of the ketone to its enol triflate followed by hydride reduction gave unsaturated ester 13 (Scott et al. *J. Am. Chem. Soc.* 1986, 108, 3033; incorporated herein by reference). Transformation of the ester in 13 to the corresponding Weimeb amide (Williams et al. *Tetrahedron Lett.* 1995, 36, 5461; incorporated herein by reference) and subsequent addition of vinylmagnesium bromide provided the divinyl ketone, 14. Lewis acid-mediated Nazarov cyclization provided the requisite cyclopentenone 6 as a single olefin isomer (for a recent review, see: Pellissier, H. *Tetrahedron* 2005, 61, 6479; incorporated herein by reference). Indeed, conjugate addition of Nagata's reagent (Nagata et al. *J. Am. Chem. Soc.* 1972, 94, 4644; incorporated herein by reference) to the enone in 6 and trapping of its derived aluminum enolate with TMSCI gave a silyl enol ether which was converted to 15 as shown (Yu et al. *Tetrahedron Lett.* 2001, 42, 369; incorporated herein by reference. The aluminum enolate derived from Nagata addition did not react usefully with a variety of triflating agents, thus prompting recourse to the more reactive potassium enolate.). Installation of the isopropyl group via Negishi coupling (notably, to a secondary sp$^3$ center) afforded 16 (for a review, see: Negishi, E.-i. In *Metal-catalyzed Cross-Coupling Reactions*; Diederich, F.; Stang, P. J., Eds.; Wiley-VCH: New York, 1998; incorporated herein by reference). The orchestration of stereocontrolled Nagata addition with enolate trapping and cross-coupling has apparently not been widely practiced. Conversion of the nitrile to the corresponding methyl ester and deketalization provided cyclohexanone 7.

Figure 3:
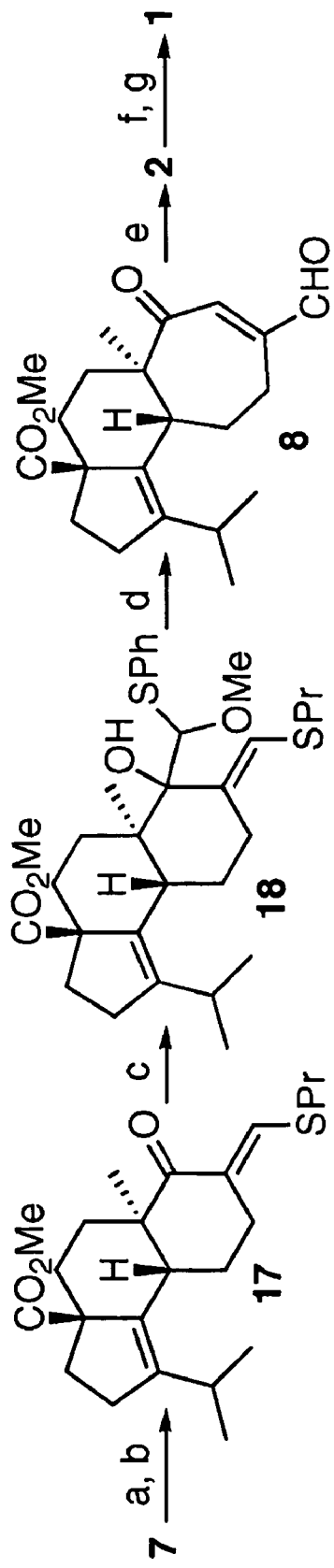
FIG. 3 shows the synthesis of scabronine G from intermediate 7.

The stage was now set for further elaboration to scabronine G. Ketone 7 was converted to thiopropylmethylidene intermediate 17 in two steps (FIG. 3). Addition of lithiated methoxymethyl phenyl sulfide afforded diastereomeric alcohols 18 which, upon treatment with HgCl$_2$ in acidic medium, underwent ring expansion to afford the cross-conjugated cycloheptenone 8 (Guerrero et al. *Tetrahedron Lett.* 1990, 31, 1873; incorporated herein by reference). Thermodynamically favored isomerization of the olefin in 8 afforded scabronine G methyl ester (2), whose spectral data were identical to those derived from natural sources. The natural product itself (1) was accessed, after chemoselective protection of the aldehyde function, by saponification of the ester and subsequent hydrolysis of the dioxolane moiety.

Figure 4:
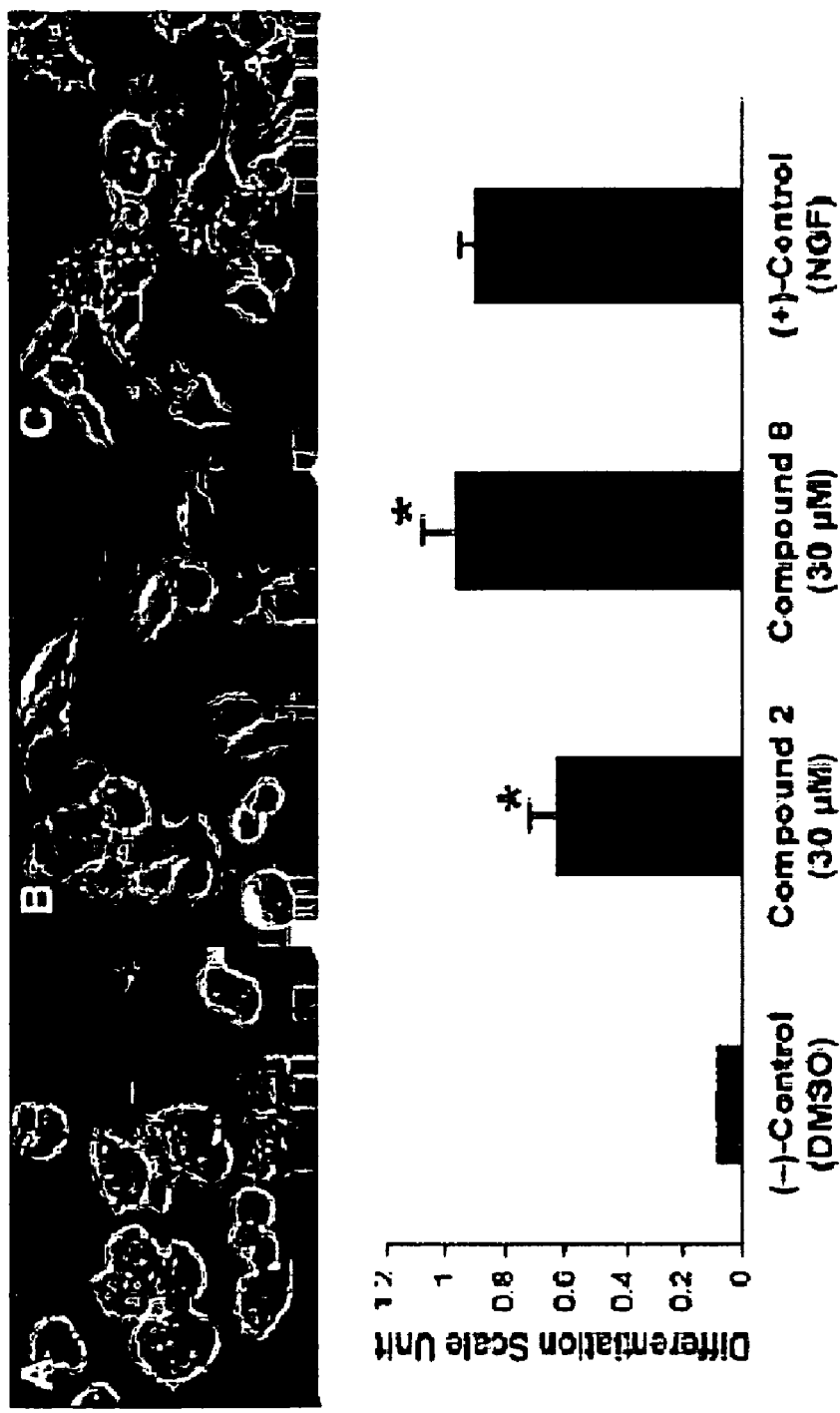
FIG. 4 shows images of differentiation and neurite outgrowth of PC-12 cells after treatment with the 1321N1 cell culture medium conditioned by: (A) DMSO (negative control), (B) scabronine G methyl ester (2, 30 μM), and (C) compound 8 (30 μM), and graphical evaluation of neurite outgrowth of PC-12 cells (*P<0.001 relative to DMSO control).

Fully synthetic scabronine C methyl ester (2) effectively enhanced the biosynthesis and secretion of neurotrophic factors from 1321N1 human glial cells. In turn, significant neurite outgrowth of PC-12 cells was observed after treatment with the conditioned 1321N1 cell culture medium (FIG. 4). To our delight, synthetic intermediate 8, a cross-conjugated analogue of 2, displayed greater activity as evidenced by increased neurite length. These effects were comparable to those produced by direct exposure of PC-12 cells to purified NGF (50 ng/mL, see graph). Very small differences in neurite outgrowth may enable otherwise failed synapses to be fruitful. The ability of 2 and, particularly 8, to extend the length of pre-existing neurites invites the study of their applicability in neurodegenerative disorders.

In summary, the first total synthesis of scabronine G, in optically pure form, has been achieved in a high-yielding sequence from readily available materials. We emphasize that this sequence lends itself to both multi-gram scale-up and to molecular modification. Moreover, it was demonstrated that an olefin isomer showed a more efficacious activity profile.

Experimentals

General Considerations. Unless otherwise stated, all non-aqueous reactions were carried out under an atmosphere of dry argon in dried glassware. When necessary, solvents and reagents were dried prior to use. Toluene, benzene, tetrahydrofuran, diethyl ether, and dichloromethane were dried and using a Solv-Tek, Inc. solvent purification system. All other solvents were of anhydrous quality purchased from Aldrich Chemical Co. and used as received. Triethylamine and TMSCI were distilled from calcium hydride under an inert atmosphere prior to use. Commercially available starting materials and reagents were purchased from Aldrich and were used as received.

Analytical thin layer chromatography (TLC) was performed on Sigma-Aldrich 0.25 mm silica gel plates with UV indicator. Visualization was accomplished by either irradiation under a 254 nm UV lamp or by staining with an aqueous solution of ceric ammonium molybdate (CAM). Chromatography on silica gel was performed using a forced flow of the indicated solvent system on Aldrich Silica Gel (60 Å).

¹H NMR spectra were recorded on a Bruker AMX-400 (400 MHz) spectrometer. ¹³C NMR spectra were recorded on a Bruker AMX-400 (100 MHz) spectrometer. Chemical shifts are reported in ppm from tetramethylsilane (0 ppm) or with the solvent resonance as the internal standard (CDCl₃ 7.26 ppm). Data are reported as follows: chemical shift, multiplicity (s=singlet, d=doublet, t=triplet, q=quartet, br=broad, m=multiplet), coupling constants, and number of protons. Infrared spectra were taken on a Perkin-Elmer 1600 FT-IR spectrometer using thin neat film deposition on NaCl plates. Infrared peaks are reported in cm¹. Mass spectra were acquired using a Perkin-Elmer Sciex API 100 in ionspray (a version of electron spray) mode. Melting points were obtained on an Electrothermal series IA9100 digital melting point apparatus.

Experimental Procedures:

(−)-Wieland-Miescher ketone (3), $[\alpha]^{25}_D$-98.2 (c=1.0, C₆H₆, >95% ee), was prepared according to literature procedure using D-proline as the chiral catalyst (Buchschacher, P.; Furst, A.; Gutzwiller, *J. Org. Syn., Coll. Vol. VII* 1990, 368; incorporated herein by reference). Wieland-Miescher ketone 9-ethylene ketal (4) was prepared according to the method of Demnitz, $[\alpha]^{25}_D$-78.4 (c=1.0, C₆H₆) (Ciceri, P.; Demnitz, F. W. J. *Tetrahedron Lett.* 1997, 38, 389; incorporated herein by reference).

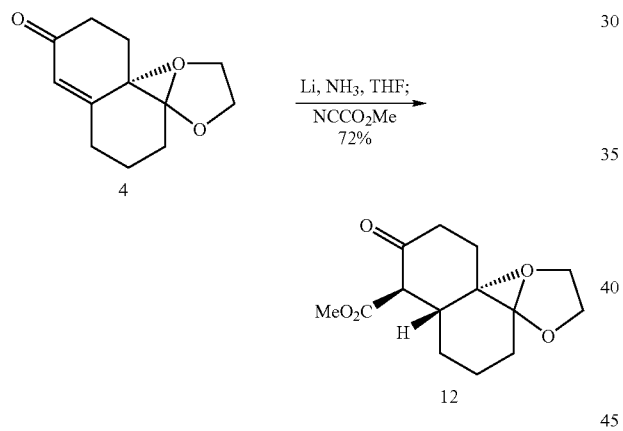

Keto-ester 12. This material was prepared by a modification of the procedure of Theodorakis and co-workers (Ling, T.; Chowdhury, C.; Kramer, B. A.; Vong, B. G.; Palladino, M. A.; Theodorakis, E. A. *J. Org Chem.* 2001, 66, 8843; incorporated herein by reference). To a solution of lithium (390 mg, 56.3 mmol) in liquid ammonia (400 mL) at −78° C was added a solution of enone 4 (5.0 g, 22.5 mmol) and t-BuOH (1.48 mL, 15.7 mmol) in Et₂O (40 mL). After 1 h, the mixture was warmed to reflux, stirred for 2 h, and quenched with isoprene (500 μL). The volatiles were removed at rt under a positive purge of argon followed by high vacuum for 10 h. The residue was suspended in Et₂O (150 mL), cooled to −78° C., and treated with methyl cyanoformate (3.0 mL, 38.2 mmol). After 1 h, the mixture was warmed to rt, stirred for 1 h, then poured into saturated NH₄Cl and extracted with Et₂O. The combined organic extracts were washed briefly with 3M NaOH, concentrated, and the residue purified by flash chromatography (33% EtOAc/hexanes) to afford keto-ester 12 (4.5 g, 72%) as a white solid. Spectroscopic and analytical data were in accord with those published.

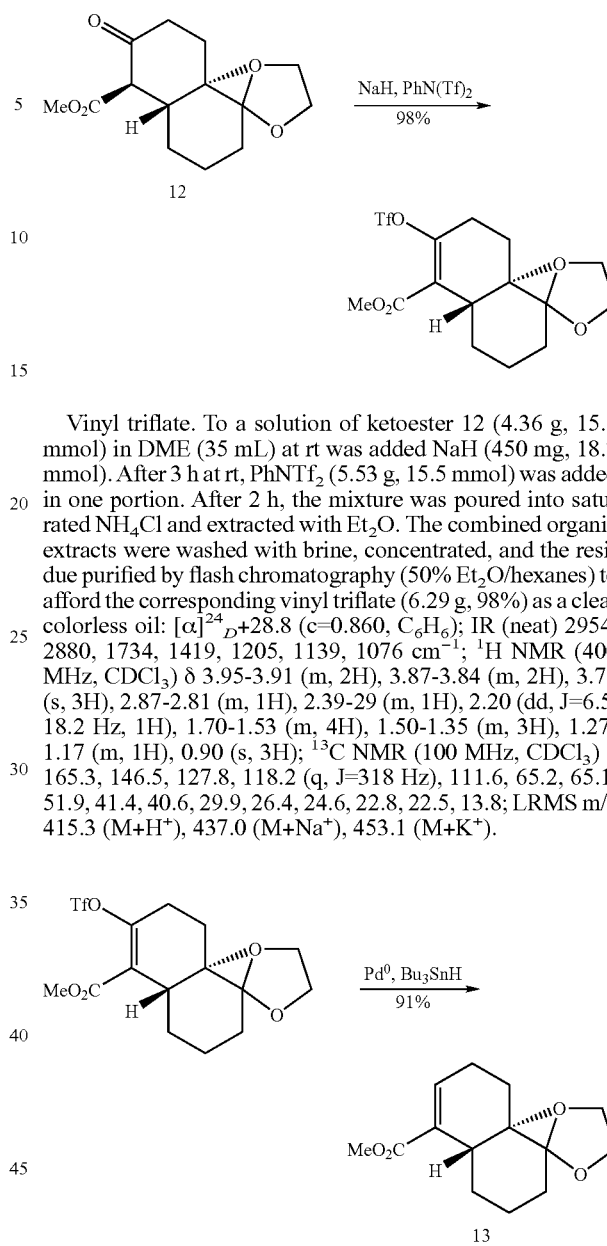

Vinyl triflate. To a solution of ketoester 12 (4.36 g, 15.5 mmol) in DME (35 mL) at rt was added NaH (450 mg, 18.7 mmol). After 3 h at rt, PhNTf₂ (5.53 g, 15.5 mmol) was added in one portion. After 2 h, the mixture was poured into saturated NH₄Cl and extracted with Et₂O. The combined organic extracts were washed with brine, concentrated, and the residue purified by flash chromatography (50% Et₂O/hexanes) to afford the corresponding vinyl triflate (6.29 g, 98%) as a clear colorless oil: $[\alpha]^{24}_D$+28.8 (c=0.860, C₆H₆); IR (neat) 2954, 2880, 1734, 1419, 1205, 1139, 1076 cm⁻¹; ¹H NMR (400 MHz, CDCl₃) δ 3.95-3.91 (m, 2H), 3.87-3.84 (m, 2H), 3.76 (s, 3H), 2.87-2.81 (m, 1H), 2.39-29 (m, 1H), 2.20 (dd, J=6.5, 18.2 Hz, 1H), 1.70-1.53 (m, 4H), 1.50-1.35 (m, 3H), 1.27-1.17 (m, 1H), 0.90 (s, 3H); ¹³C NMR (100 MHz, CDCl₃) δ 165.3, 146.5, 127.8, 118.2 (q, J=318 Hz), 111.6, 65.2, 65.1, 51.9, 41.4, 40.6, 29.9, 26.4, 24.6, 22.8, 22.5, 13.8; LRMS m/z 415.3 (M+H⁺), 437.0 (M+Na⁺), 453.1 (M+K⁺).

Unsaturated Methyl Ester 13. To a solution of the vinyl triflate (6.29 g, 15.2 mmol), LiCl (1.97 g, 46.5 mmol), and Pd(PPh₃)₄ (358 mg, 0.31 mmol) in THF (50 mL) at rt was added Bu₃SnH (5.0 mL, 18.6 mmol) dropwise over 20 min. The mixture was heated to 50° C. and stirred for 3 h, then diluted with Et₂O, washed with 10% KF and brine, concentrated, and the residue purified by flash chromatography (10-20% EtOAc/hexanes) to afford unsaturated ester 13 (3.68 g, 91%) as a clear colorless oil: $[\alpha]^{26}_D$+119.4 (c=1.10, C₆H₆); IR (neat) 2949, 2884, 1713, 1433, 1252, 1181, 1086 cm⁻¹; ¹H NMR (400 MHz, CDCl₃) δ 6.56 (dd, J=3.4, 6.7 Hz, 1H), 3.96-3.91 (m, 2H), 3.89-3.86 (m, 2H), 3.68 (s, 3H), 2.68-2.63 (m, 1H), 2.19-2.15 (m, 2H), 2.03 (dd, J=2.7, 12.9 Hz, 1H), 1.85-1.77 (m, 1H), 1.70-1.65 (m, 1H), 1.61-1.47 (m, 4H), 1.18-1.08 (m, 1H), 0.93 (s, 3H); ¹³C NMR (100 MHz, CDCl₃) δ 168.8, 136.8, 133.9, 112.5, 65.2, 65.0, 51.3, 41.1, 40.4, 30.4, 25.8, 22.9, 22.8, 22.3, 14.3; LRMS m/z 267.2 (M+H⁺), 289.1 (M+Na⁺), 305.1 (M+K⁺).

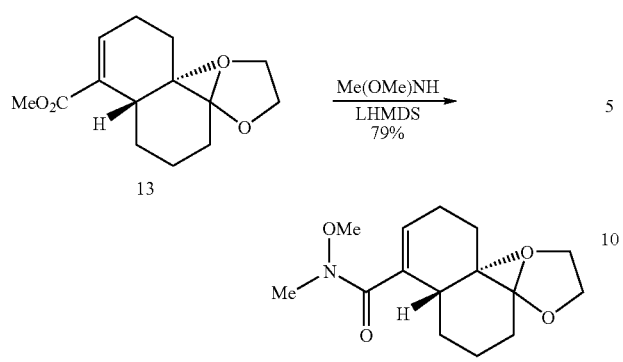

Weinreb Amide. To a solution of ester 13 (4.10 g, 15.4 mmol) and Me(OMe)NH.HCl (2.33 g, 23.9 mmol) in THF (100 mL) at −10° C. was added LHMDS (46.2 mL, 1.0 M in THF, 46.2 mmol) over 15 min. After stirring for 15 min at −10° C., the mixture was warmed to rt and stirred for 2 h. The mixture was diluted with Et$_2$O, washed with saturated NH$_4$Cl and brine, dried (MgSO$_4$), concentrated, and the residue purified by flash chromatography (100% EtOAc) to afford the corresponding Weinreb amide (3.57 g, 79%) as a clear colorless oil: [α]$^{26}_D$+57.2 (c=0.766, C$_6$H$_6$); IR (neat) 2937, 2872, 1640, 1375, 1198, 1178, 1121, 1080 cm$^{-1}$; $^1$H NMR (400 MHz, CDCl$_3$) δ 5.77 (dd, J=3.2, 6.7 Hz, 1H), 3.96-3.85 (m, 4H), 3.62 (s, 3H), 3.19 (s, 3H), 2.74-2.69 (m, 1H), 2.16-2.09 (m, 2H), 1.82-1.74 (m, 1H), 1.68-1.63 (m, 2H), 1.56-1.43 (m, 4H), 1.34-1.24 (m, 1H), 0.98 (s, 3H); $^{13}$C NMR (100 MHz, CDCl$_3$) δ 137.2, 126.5, 112.4, 65.2, 65.1, 60.8, 40.9, 40.7, 30.5, 26.1, 22.9, 22.8, 22.4, 13.8; LRMS m/z 296.2 (M+H$^+$), 318.1 (M+Na$^+$), 334.0 (M+K$^+$).

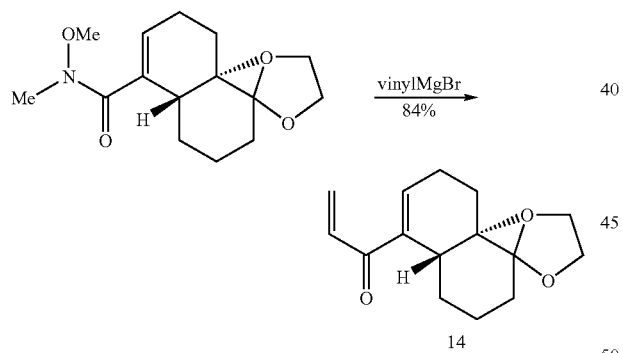

Divinyl Ketone 14. To a solution of the Weinreb amide (470 mg, 1.59 mmol) in THF (10 mL) at −20° C. was added vinylMgBr (4.78 mL, 1.0 M in THF, 4.78 mmol). The mixture was warmed to rt, stirred for 2 h, poured into saturated NH$_4$Cl, and extracted with Et$_2$O. The combined organic extracts were washed with brine, concentrated, and the residue purified by flash chromatography (33% EtOAc/hexanes) to afford divinyl ketone 14 (351 mg, 84%) as a white solid: mp 64.5-65.0° C.; [α]$^{25}_D$+186.2 (c=0.850, C$_6$H$_6$); IR (film) 2940, 2873, 1653, 1603, 1399, 1176, 1121, 1075 cm$^{-1}$; $^1$H NMR (400 MHz, CDCl$_3$) δ 6.56 (dd, J=10.6, 17.3 Hz, 1H), 6.31 (dd, J=3.4, 6.8 Hz, 1H), 6.16 (dd, J=1.1, 17.3 Hz, 1H), 5.78 (dd, J=1.1, 10.6 Hz, 1H), 3.97-3.87 (m, 4H), 2.81-2.75 (m, 1H), 2.27-2.21 (m, 2H), 1.89-1.84 (m, 1H), 1.79 (dd, J=5.1, 13.9 Hz, 1H), 1.67-1.51 (m, 5H), 1.11-1.01 (m, 1H), 0.99 (s, 3H); $^{13}$C NMR (100 MHz, CDCl$_3$) δ 195.2, 142.3, 135.6 (2C), 129.0, 112.5, 65.2, 65.1, 41.1, 40.4, 30.4, 25.8, 23.0, 22.9, 22.0, 14.3; LRMS m/z 263.1 (M+H$^+$), 284.9 (M+Na$^+$), 301.1 (M+K$^+$).

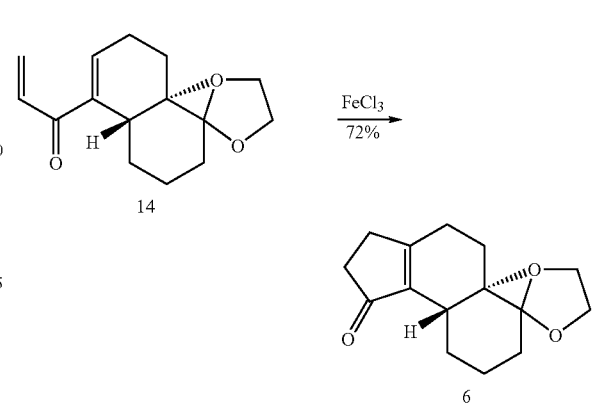

Cyclopentenone 6. To a solution of divinyl ketone 14 (2.40 g, 9.2 mmol) in CH$_2$Cl$_2$ (250 mL) at rt was added FeCl$_3$ (1.63 g, 10.1 mmol) in one portion. After 3 h at rt, the mixture was treated with ice-cold saturated NaHCO$_3$. The separated organic extract was washed with brine, dried (Na$_2$SO$_4$), concentrated, and the residue purified by flash chromatography (33% EtOAc/hexanes) to afford cyclopentenone 6 (1.73 g, 72%) as a clear colorless oil: [α]$^{26}_D$+104.3 (c=0.770, C$_6$H$_6$); IR (neat) 2948, 2884, 1691, 1631, 1442, 1385, 1302, 1179, 1087 cm$^{-1}$; $^1$H NMR (400 MHz, CDCl$_3$) δ 3.98-3.87 (m, 4H), 2.72 (dd, J=2.8, 13.5 Hz, 1H), 2.56 (ddd, J=2.9, 5.6, 12.9 Hz, 1H), 2.42-2.32 (m, 5H), 1.82-1.46 (m, 7H), 1.21-1.10 (m, 1H), 0.88 (s, 3H); $^{13}$C NMR (100 MHz, CDCl$_3$) δ 209.4, 173.1, 138.7, 112.4, 65.1, 65.0, 41.6, 39.7, 35.6, 30.4, 28.9, 26.4, 26.3, 22.9, 20.6, 14.3; LRMS m/z 263.0 (M+H$^+$), 285.1 (M+Na$^+$), 301.1 (M+K$^+$).

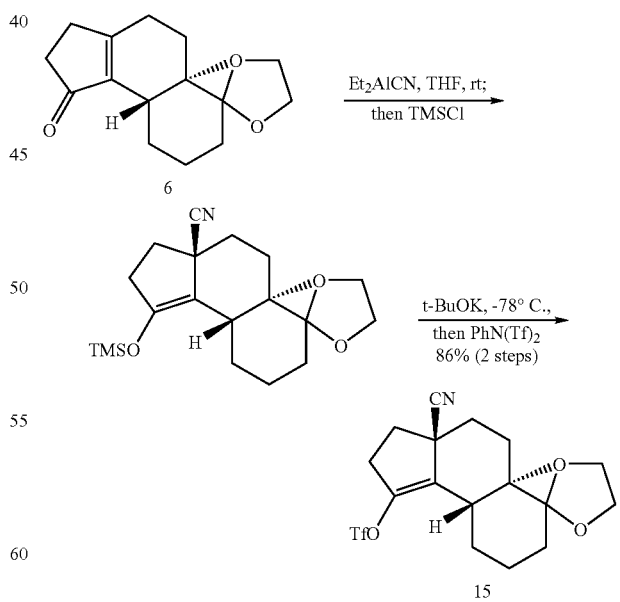

Vinyl triflate 15. To a solution of cyclopentenone 6 (1.70 g, 6.5 mmol) in THF (100 mL) at rt was added Et$_2$AlCN (13.0 mL, 1.0 M in toluene, 13.0 mmol). After 20 min, Et$_3$N (4.5 mL, 32.4 mmol) was added, followed by TMSCl (2.5 mL, 19.5 mmol). After 2.5 h, the mixture was diluted with Et₂O, washed with saturated NaHCO₃ and brine, dried (Na₂SO₄), concentrated, and the crude silyl enol ether placed under high vacuum overnight. This material (2.34 g) was dissolved in THF (100 mL), cooled to −78° C., and treated with t-BuOK (8.0 mL, 1.0 M in THF, 8.0 mmol). After 20 min, N-(5-chloro-2-pyridyl)triflimide (3.06 g, 7.8 mmol) was added in one portion, and the mixture was stirred at −78° C. for 2 h. The mixture was poured into brine and extracted with Et₂O. The combined organic extracts were dried (Na₂SO₄), concentrated, and the residue purified by flash chromatography (20% EtOAc/hexanes) to afford vinyl triflate 15 (2.34 g, 86%) as a white solid: mp 81.5-82.5° C.; [α]²⁵_D −19.5 (c=0.815, C₆H₆); IR (film) 2954, 2876, 2231, 1420, 1216, 1138, 1101 cm⁻¹; ¹H NMR (400 MHz, CDCl₃) δ 3.97-3.84 (m, 4H), 2.86 (ddd, J=3.7, 8.1, 16.7 Hz, 1H), 2.75-2.65 (m, 2H), 2.50 (ddd, J=3.2, 9.4, 13.3 Hz, 1H), 2.13 (ddd, J=3.4, 3.4, 13.5 Hz, 1H), 2.06-1.92 (m, 2H), 1.86-1.82 (m, 1H), 1.76-1.62 (m, 4H), 1.59-1.48 (m, 3H), 0.95 (s, 3H); ¹³C NMR (100 MHz, CDCl₃) δ 144.1, 129.2, 121.9, 118.1 (q, J=318 Hz), 111.2, 65.2, 65.1, 45.4, 44.1, 42.3, 34.4, 32.3, 29.9, 29.8, 27.7, 22.8, 22.4, 14.9; LRMS m/z 422.1 (M+H⁺), 444.1 (M+Na⁺), 460.2 (M+K⁺).

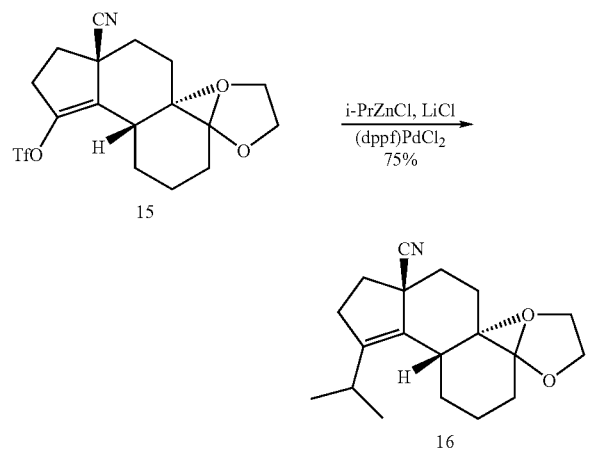

Cross-Coupled Alkene 16. To a solution of anhydrous ZnCl₂ (22.0 mL, 0.5 M in THF, 11.0 mmol) at 0° C. was added i-PrMgCl (5.5 mL, 2.0 M in THF, 11.0 mmol). After 1 h, stirring was ceased and the precipitates were allowed to settle. One-half (13.0 mL) of this solution was added via cannula to a dry mixture of 15 (1.15 g, 2.73 mmol), LiCl (347 mg, 8.19 mmol) and (dppf)PdCl₂ (223 mg, 0.273 mmol), heated to 55° C., and stirred for 24 h. The mixture was poured into saturated NH₄Cl and extracted with Et₂O. The combined organic extracts were washed with brine, dried (Na₂SO₄), concentrated, and the residue purified by flash chromatography (20% EtOAc/hexanes) to afford 16 (647 mg, 75%) as white solid: mp 131-132° C.; [α]²⁵_D +23.1 (c=0.925, C₆H₆); IR (film) 2953, 2871, 2245, 1460, 1191, 1132, 1095 cm⁻¹; ¹H NMR (400 MHz, CDCl₃) δ 3.99-3.86 (m, 4H), 3.11 (septet, J=6.8 Hz, 1H), 2.75-2.72 (m, 1H), 2.59-2.33 (m, 2H), 2.23-2.00 (m, 2H), 1.88-1.85 (m, 1H), 1.78-1.65 (m, 4H), 1.60-1.37 (m, 5H), 0.99 (d, J=6.8 Hz, 3H), 0.97 (d, J=6.8 Hz, 3H), 0.93 (s, 3H); ¹³C NMR (100 MHz, CDCl₃) δ 145.6, 129.8, 124.4, 111.9, 65.2, 65.0, 50.6, 44.4, 44.3, 34.7, 34.6, 30.3, 30.0, 28.2, 26.4, 25.4, 22.9, 21.9, 21.2, 15.2; LRMS m/z 316.2 (M+H⁺), 338.0 (M+Na⁺), 354.2 (M+K⁺).

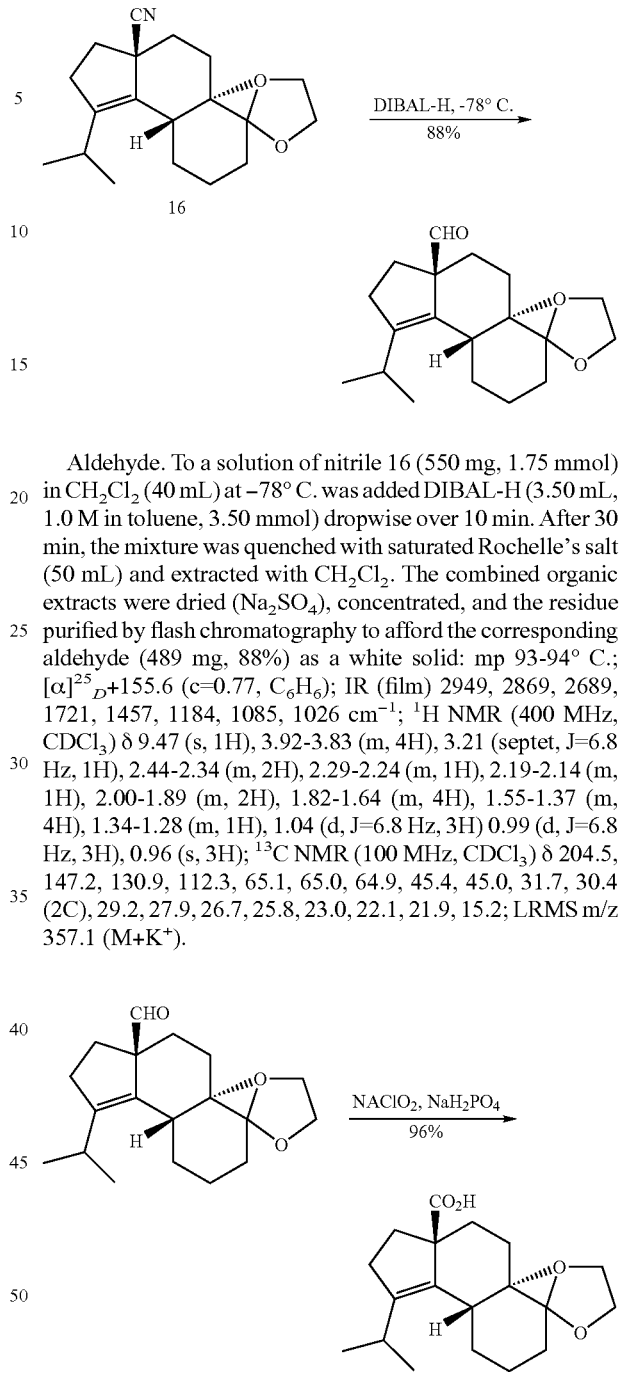

Aldehyde. To a solution of nitrile 16 (550 mg, 1.75 mmol) in CH₂Cl₂ (40 mL) at −78° C. was added DIBAL-H (3.50 mL, 1.0 M in toluene, 3.50 mmol) dropwise over 10 min. After 30 min, the mixture was quenched with saturated Rochelle's salt (50 mL) and extracted with CH₂Cl₂. The combined organic extracts were dried (Na₂SO₄), concentrated, and the residue purified by flash chromatography to afford the corresponding aldehyde (489 mg, 88%) as a white solid: mp 93-94° C.; [α]²⁵_D +155.6 (c=0.77, C₆H₆); IR (film) 2949, 2869, 2689, 1721, 1457, 1184, 1085, 1026 cm⁻¹; ¹H NMR (400 MHz, CDCl₃) δ 9.47 (s, 1H), 3.92-3.83 (m, 4H), 3.21 (septet, J=6.8 Hz, 1H), 2.44-2.34 (m, 2H), 2.29-2.24 (m, 1H), 2.19-2.14 (m, 1H), 2.00-1.89 (m, 2H), 1.82-1.64 (m, 4H), 1.55-1.37 (m, 4H), 1.34-1.28 (m, 1H), 1.04 (d, J=6.8 Hz, 3H) 0.99 (d, J=6.8 Hz, 3H), 0.96 (s, 3H); ¹³C NMR (100 MHz, CDCl₃) δ 204.5, 147.2, 130.9, 112.3, 65.1, 65.0, 64.9, 45.4, 45.0, 31.7, 30.4 (2C), 29.2, 27.9, 26.7, 25.8, 23.0, 22.1, 21.9, 15.2; LRMS m/z 357.1 (M+K⁺).

Carboxylic Acid. To a mixture of the aldehyde (474 mg, 1.49 mmol), 2-methyl-2-butene (10.0 mL, 2.0 M in THF, 20.0 mmol), t-BuOH (20 mL) and H₂O (10 mL) at rt was added NaH₂PO₄·H₂O (1.03 g, 7.45 mmol) followed by NaClO₂ (842 mg, 7.45 mmol). After 40 min, the mixture was poured into brine and extracted with Et₂O. The combined organic extracts were dried (Na₂SO₄) and concentrated to afford the corresponding carboxylic acid (480 mg, 96%) as a white solid: mp 94.1-95.2° C.; [α]²⁵_D +28.7 (c=0.82, C₆H₆); IR (film) 3050 (br), 2951, 2870, 1695, 1457, 1186, 1128, 1082 cm⁻¹; ¹H NMR (400 MHz, CDCl₃) δ 3.86-3.73 (m, 4H), 3.07 (septet, J=6.8 Hz, 1H), 2.39-2.26 (m, 2H), 2.21-2.15 (m, 1H), 2.09-2.02 (m, 1H), 1.82-1.75 (m, 1H), 1.74-1.50 (m, 5H), 1.46-1.20 (m, 5H), 0.92 (d, J=6.8 Hz, 3H), 0.89 (s, 3H), 0.88 (d, J=6.8 Hz, 3H); $^{13}$C NMR (100 MHz, CDCl$_3$) δ 182.7, 145.3, 132.0, 112.5, 65.2, 64.9, 60.7, 45.3, 44.3, 35.8, 32.7, 30.5, 30.4, 28.7, 26.5, 25.8, 23.2, 22.2, 21.4, 15.3; LRMS m/z 335.2 (M+H$^+$), 357.2 (M+Na$^+$), 373.2 (M+K$^+$).

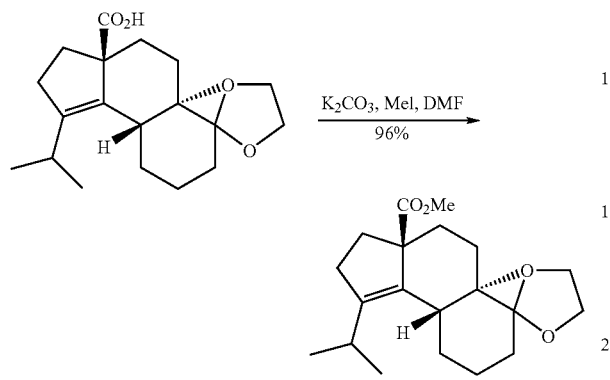

Methyl Ester. To a solution of the carboxylic acid (480 mg, 1.44 mmol) in DMF (20 mL) and MeI (4 mL) at rt was added K$_2$CO$_3$ (1.03 g, 7.45 mmol) in one portion. After 2 h, the mixture was poured into H$_2$O and extracted with Et2O. The organic extract was washed with brine, dried (Na$_2$SO$_4$) and concentrated to afford the methyl ester (490 mg, 99%) as a clear colorless oil: $[\alpha]^{25}_D$+19.6 (c=0.85, C$_6$H$_6$); IR (neat) 2950, 2870, 1727, 1478, 1182, 1082 cm$^{-1}$; $^1$H NMR (400 MHz, CDCl$_3$) δ 3.94-3.83 (m, 4H), 3.67 (s, 3H), 3.15 (septet, J=6.8 Hz, 1H), 2.48-2.19 (m, 3H), 1.99 (ddd, J=4.0, 8.5, 12.9 Hz, 1H), 1.90-1.87 (m, 1H), 1.78-1.30 (m, 10H), 1.01 (d, J=6.8 Hz, 3H), 0.98 (d, J=6.8 Hz, 3H), 0.96 (s, 3H); $^{13}$C NMR (100 MHz, CDCl$_3$) δ 177.8, 144.4, 132.4, 112.4, 65.2, 64.9, 61.0, 51.8, 45.2, 44.4, 35.4, 33.0. 30.5, 30.3, 28.8, 26.4, 25.8, 23.2, 22.1, 21.4, 15.4; LRMS m/z 371.1 (M+Na$^+$), 387.3 (M+K$^+$).

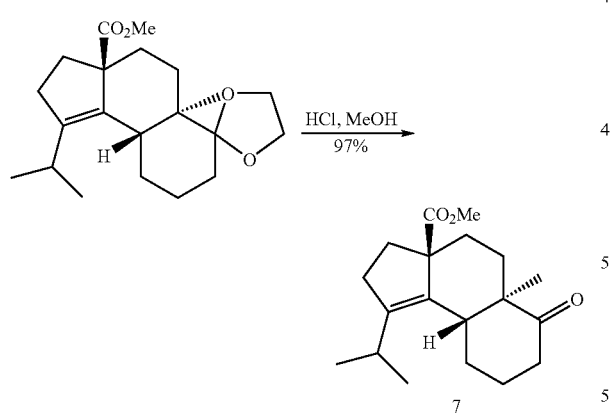

Cyclohexanone 7. To a solution of the dioxolane (480 mg, 1.38 mmol) in MeOH (30 mL) at rt was added HCl (10 mL, 3.0 M in H$_2$O). After 3 h at rt, the mixture was poured into brine and extracted with Et$_2$O. The combined organic extracts were concentrated and the residue purified by flash chromatography (20% EtOAc/hexanes) to afford cyclohexanone 7 (415 mg, 97%) as a clear colorless oil: $[\alpha]^{25}_D$+25.8 (c=0.74, C$_6$H$_6$); IR (neat) 2944, 2861, 1725, 1702, 1449, 1190, 1161 cm$^{-1}$; $^1$H NMR (400 MHz, CDCl$_3$) δ 3.61 (s, 3H), 3.14 (septet, J=6.8 Hz, 1H), 2.59 (dt, J=6.1, 14.3 Hz, 1H), 2.41- 2.30 (m, 4H), 2.24-2.19 (m, 1H), 2.10-1.98 (m, 4H), 1.67-1.52 (m, 4H), 1.36 (dt, J=5.0, 13.4 Hz, 1H), 1.06 (s, 3H), 1.02 (d, J=6.8 Hz, 3H), 0.99 (d, J=6.8 Hz, 3H); $^{13}$C NMR (100 MHz, CDCl$_3$) δ 215.3, 177.2, 146.0, 130.5, 60.8, 51.7, 50.0, 48.5, 37.6, 35.1, 32.6, 31.5, 30.2, 26.5, 26.4, 25.5, 22.1, 21.4, 17.2; LRMS m/z 305.2 (M+H$^+$), 327.0 (M+Na$^+$), 343.0 (M+K$^+$).

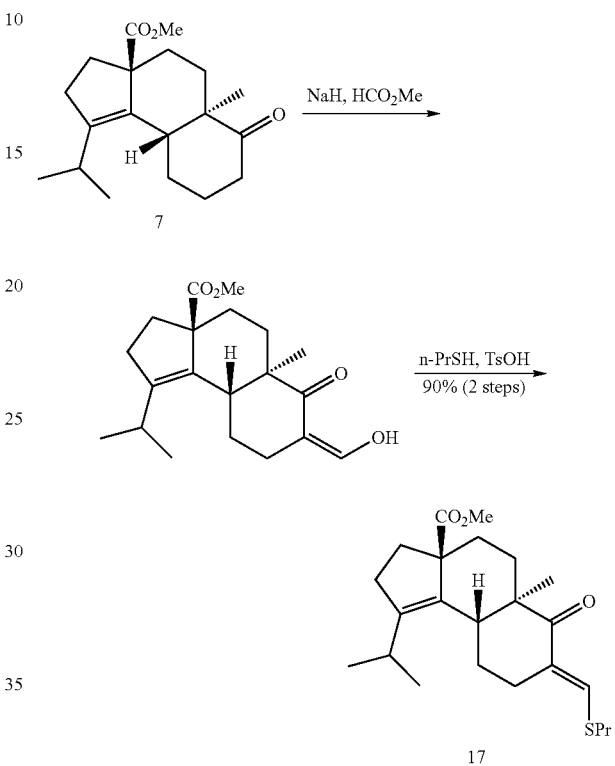

Thiopropylmethylidene 17. To a 100 mL flask charged with NaH (475 mg, 19.8 mmol) at 0° C. was added methyl formate (20 mL). After stirring at 0° C. for 1 h, a solution of the ketone (400 mg, 1.32 mmol) in DME (20 mL) was added via cannula. After 30 min, the mixture was warmed to rt and stirred for 6 h. The mixture was poured into saturated NH$_4$Cl and extracted with Et$_2$O. The combined organic extracts were washed with brine, dried (Na$_2$SO$_4$), and concentrated to afford the crude formylated ketone (424 mg) which, due to its instability, required use without purification. A portion of this material (60 mg, 0.18 mmol), TsOH.H$_2$O (34 mg, 0.18 mmol) and n-PrSH (1.0 mL) in benzene (10 mL) was stirred at 50° C. for 3 h. The volatiles were removed under reduced pressure and the residue purified by flash chromatography (20% EtOAc/hexanes) to afford 17 (66 mg, 93%) as a pale yellow oil: $[\alpha]^{24}_D$-37.5 (c=0.665, C$_6$H$_6$); IR (neat) 2956, 2870, 1726, 1662, 1539, 1456, 1243, 1170 cm$^{-1}$; $^1$H NMR (400 MHz, CDCl$_3$) δ 7.53 (s, 1H), 3.65 (s, 3H), 3.11 (septet. J=6.8 Hz, 1H), 2.81 (t, J=7.2 Hz, 2H), 2.64-2.52 (m, 2H), 2.46-2.40 (m, 2H), 2.33 (m, 1H), 2.24-2.19 (m, 3H), 2.09-1.98 (m, 3H), 1.71 (q, J=7.2 Hz, 3H), 1.61 (m, 2H), 1.51-1.40 (m, 2H), 1.03 (d, J=6.8 Hz, 3H), 1.00 (s, 3H), 0.99 (d, J=6.8 Hz, 3H); $^{13}$C NMR (100 MHz, CDCl$_3$) δ 201.0, 177.4, 145.4, 143.1, 131.4, 128.8, 60.7, 51.8, 47.6, 45.2, 36.6, 35.0, 32.9 (2C), 30.3, 27.7, 26.5, 23.9, 22.8, 21.9, 21.6, 17.6, 13.0; LRMS m/z 391.0 (M+H$^+$), 413.2 (M+Na$^+$), 429.3 (M+K$^+$).

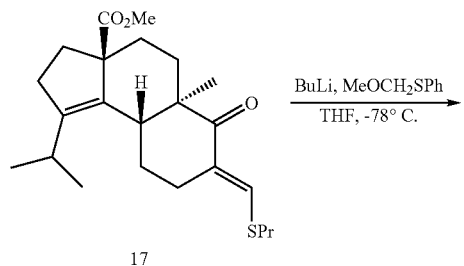 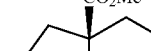

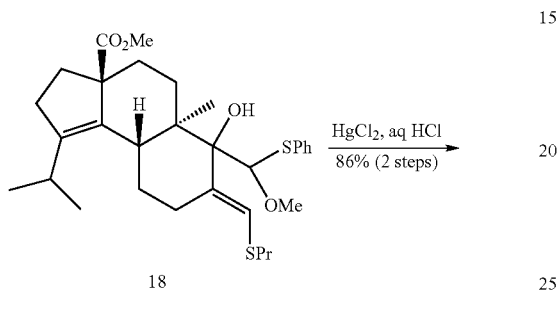 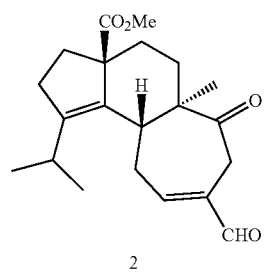

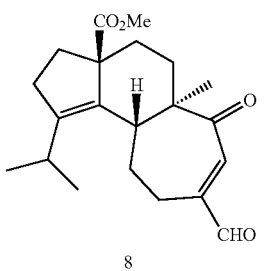

Cycloheptenone 8. To a solution of methoxymethyl phenyl sulfide (150 μL, 1.03 mmol) in THF (5 mL) at −30° C. was added n-BuLi (640 μL, 1.6 M in hexanes, 1.03 mmol). After 1 h, a 1.5 mL aliquot was added rapidly to a solution of 17 (40 mg, 0.10 mmol) in THF (5 mL) at −78° C. After 30 min, the reaction mixture was quenched with saturated NH$_4$Cl, extracted with Et$_2$O, and concentrated to afford crude diastereomeric alcohols 18, which was treated with HgCl$_2$ (271 mg, 1.0 mmol) and 3% HCl/H$_2$O (1 mL) in MeCN (5 mL) for 2 h at 80° C. The mixture was poured into saturated NH$_4$Cl and extracted with Et$_2$O. The combined organic extracts were washed with brine, concentrated, and the residue purified by flash chromatography (25% EtOAc/hexanes) to afford cycloheptenone 8 (29 mg, 86%) as a clear colorless oil: $[\alpha]^{26}_D$−119.2(c=0.587,C$_6$H$_6$); IR (neat) 2953, 1869, 1726, 1696, 1456, 1176, 1076 cm$^{-}$; $^1$H NMR (400 MHz, CDCl$_3$) δ 9.56 (s, 1H), 6.62 (s, 1H), 3.65 (s, 3H), 2.95 (septet, J=6.8 Hz, 1H), 2.71-2.56 (m, 2H), 2.45 (ddd, J=4.0, 6.6, 13.3 Hz, 1H), 2.36-2.24 (m, 3H), 2.06-1.92 (m, 2H), 1.85-1.77 (m, 1H), 1.70-1.64 (m, 1H), 1.52-1.42 (m, 3H), 1.14 (s, 3H), 1.05 (d, J=6.8 Hz, 3H), 1.01 (d, J=6.8 Hz, 3H); $^{13}$C NMR (100 MHz, CDCl$_3$) δ 208.9, 194.7, 177.2, 146.1, 144.9, 144.1, 132.1, 61.7, 54.3, 51.9, 45.6, 34.6, 34.0, 31.9, 30.1, 27.2, 27.0, 25.3, 21.7, 21.4, 15.8; LRMS m/z 367.1 (M+Na$^+$), 383.2 (M+K$^+$).

Scabronine G Methyl Ester (2). A solution of 8 (10.0 mg, 0.029 mmol) and DBU (10 μL) in benzene (4 mL) was heated at 75° C. for 90 min. The volatiles were removed under reduced pressure and the residue purified by flash chromatography (25% EtOAc/hexanes) to afford scabronine G methyl ester (2) (10.0 mg, 100%) as a clear colorless oil: $[\alpha]^{24}_D$−64.3 (c=0.51, C$_6$H$_6$); IR (neat) 2952, 1724, 1707, 1689, 1440, 1193, 1145, 1071 cm$^{-1}$; $^1$H NMR (400 MHz, CDCl$_3$) δ 9.53 (s, 1H), 6.70 (dt, J=2.6, 5.9 Hz, 1H), 3.69 (s, 3H), 3.64-3.60 (m, 1H), 3.44 (d, J=14.0 Hz, 1H), 3.22 (br d, J=12.5 Hz, 1H), 3.03 (br dd, J=6.3, 19.2 Hz, 1H), 2.97 (septet, J=6.8 Hz, 1H), 2.86 (m, 1H), 2.50-2.45 (m, 2H), 2.32 (ddd, J=2.6, 4.0, 13.5 Hz, 1H), 2.09 (ddd, J=6.0, 8.8, 13.5 Hz, 1H), 1.86 (dt, J=4.0, 13.5 Hz, 1H), 1.67 (ddd, J=6.9, 8.8, 13.5 Hz, 1H), 1.54 (dt, J=4.2, 13.5 Hz, 1H), 1.35 (ddd, J=2.6, 4.1, 13.5 Hz, 1H) 1.07 (d, J=6.8 Hz, 3H), 1.07 (s, 3H), 1.04 (d, J=6.8 Hz, 3H); $^{13}$C NMR (100 MHz, CDCl$_3$) δ 210.2, 192.2, 177.1, 152.8, 145.2, 135.8, 130.3, 61.4, 54.2, 52.1, 41.8, 34.4, 34.3, 33.9, 32.3, 31.5, 30.2, 27.2, 21.7, 21.5, 12.9; LRMS m/z 367.2 (M+Na$^+$), 383.1 (M+K$^+$).

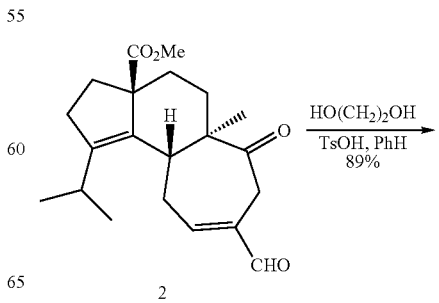

-continued

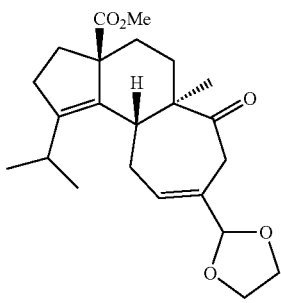

Dioxolane. A mixture of 2 (10.0 mg, 0.029 mmol), TsOH.H2O (5.5 mg, 0.029 mmol) and ethylene glycol (500 μL) in benzene (2 mL) was stirred at rt for 20 h. The mixture was poured into saturated NaHCO3 and extracted with Et2O. The combined organic extracts were washed with brine, concentrated, and the residue purified by flash chromatography (50% EtOAc/hexanes) to afford the corresponding dioxolane (10.0 mg, 89%) as a clear colorless oil: $[\alpha]25D-68.2$ (c=0.503, C6H6); IR (neat) 2951, 1725, 1706, 1456, 1190, 1084, 1044 cm−1; 1H NMR (400 MHz, CDCl3) ☐ 5.86 (dt, J=3.0, 5.9 Hz, 1H), 5.09 (s, 1H), 4.10-3.88 (m, 4H), 3.72 (m, 1H), 3.69 (s, 3H), 3.14 (br d, J=13.3 Hz, 1H), 2.97 (septet, J=6.8 Hz, 1H), 2.82 (d, J=13.5 Hz, 1H), 2.76-2.70 (m, 1H), 2.65-2.56 (m, 1H), 2.39-2.29 (m, 1H), 2.31 (ddd, J=2.6, 4.1, 13.4 Hz, 1H), 2.07 (ddd, J=5.2, 9.1, 13.5 Hz, 1H), 1.84 (dt, J=4.5, 13.5 Hz, 1H), 1.63 (m, 2H), 1.50 (dt, J=4.2, 13.5 Hz, 1H), 1.32 (ddd, J=2.6, 4.1, 13.5 Hz, 1H), 1.06 (s, 3H), 1.04 (d, J=6.8 Hz, 3H), 1.01 (d, J=6.8 Hz, 3H); 13C NMR (100 MHz, CDCl3) ☐210.9, 177.2, 144.8, 131.5, 131.1, 129.1, 107.0, 65.4, 65.3, 61.3, 53.9, 52.1, 42.2, 35.7, 34.6, 34.4, 32.4, 30.3, 30.2, 27.0, 21.7, 21.6, 13.1; LRMS m/z 389.2 (M+H+), 411.1 (M+Na+), 427.3 (M+K+).

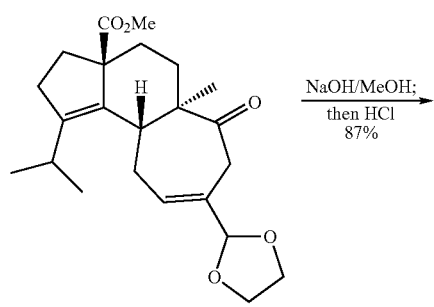

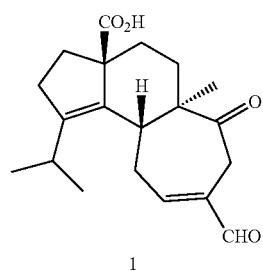

1

Scabronine G (1). A solution of the dioxolane (10.0 mg, 0.026 mmol) in MeOH (1 mL) and NaOH (1 mL, 2.0 M in H2O) were heated at 55° C. for 7 h. The mixture was cooled to rt, treated with HCl (6.0 M in H2O) to pH 0, and stirred at rt for 30 min. The mixture was poured into H2O and extracted with Et2O. The combined organic extracts were concentrated and the residue purified flash chromatography (5% MeOH/CHCl3) to afford scabronine G (1): $[\alpha]^{25}_D$−28.3 (c=0.30, C6H6); IR (neat) 3300 (b), 2931, 2872, 1698, 1455, 1437, 1255, 1214, 1143, 1073 cm−1; 1H NMR (400 MHz, CDCl3) δ 9.37 (s, 1H), 6.72 (dt, J=3.0, 5.9 Hz, 1H), 3.67 (dd, J=1.0, 13.5 Hz, 1H), 3.47 (d, J=14.0 Hz, 1H), 3.28 (br d, J=12.2 Hz, 1H), 3.05 (dd, J=6.5, 19.0 Hz, 1H), 2.99 (septet, J=6.8 Hz, 1H), 2.88 (m, 1H), 2.55-2.48 (m, 2H), 2.34 (ddd, J=2.6, 4.2, 13.5 Hz, 1H), 2.25 (ddd, J=4.6, 9.0, 13.3 Hz, 1H), 1.95 (dt, J=4.2, 13.5 Hz, 1H), 1.73 (ddd, J=6.6, 9.2, 13.4 Hz, 1H), 1.56 (dt, J=4.2, 13.5 Hz, 1H), 1.38 (ddd, J=2.6, 4.2, 13.5 Hz, 1H), 1.09 (s, 3H), 1.07 (d, J=6.8 Hz, 3H), 1.05 (d, J=6.8 Hz, 3H); 13C NMR (100 MHz, CDCl3) δ 210.1, 192.3, 181.7, 152.7, 146.1, 135.9, 129.8, 61.1, 54.2, 41.9, 34.7, 34.2, 34.0, 32.2, 31.5, 30.4, 27.2, 21.7, 21.6, 12.9; LRMS m/z 352.2 (M+Na+).

Cell Culture and Compound Assay:

The 1321N1 human astrocytoma cells were cultured in Dulbecco's modified Eagles's medium (DMEM) supplemented with 2 mM L-Glutamine and 10% fetal bovine serum (FBS). PC-12 cells were grown in F-12K medium supplemented with 15% horse serum and 2.5% FBS. For compound treatment, 1321N1 cells were incubated with compounds 2 and 8 at 30 μM for 48 hours in DMEM medium. The resulting conditioned media from the 1321N1 cells were used to culture PC-12 cell for induction of PC-12 neurite outgrowth. After 3 days incubation, PC-12 cells were washed with phosphate-buffered saline (PBS) and fixed with 4% paraformaldeyde. Neurites were observed under a phase-contrast ECLIPSE TE2000-S Nikon microscope.

Evaluation of Neurite Outgrowth:

The differentiation of PC-12 cells was scored as follows: cells without neurites were scored 0; cells with neurites as long as one cell body diameter were scored 1; cells with neurites 2-3 times longer than their cell body diameter were scored 2; and cells with neurites that were extremely long or forming a network were scored 3. The mean of differentiation scores were obtained from 200 cells (4 wells) under the phase-contrast microscope. Data are expressed as means±S.E.M (standard error of mean). Values represent the Means±S.E.M. for four wells. Compounds 2 and 8 both significantly induced neurite outgrowth compare to the DMSO control (*P<0.001). Compound 8 had a greater potency than compound 2, which had the same degree of neurite outgrowth as that of 50 ng/mL of NGF.

Synthesis of Analogues:

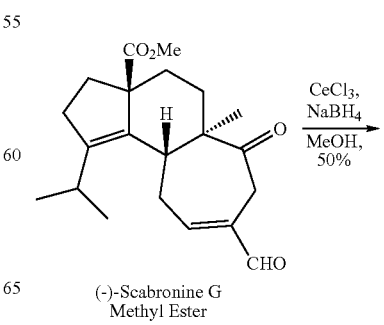

(-)-Scabronine G
Methyl Ester

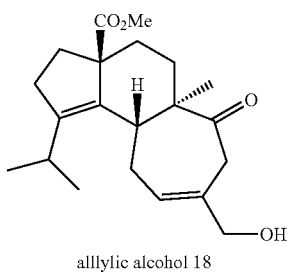

alllylic alcohol 18

Allylic Alcohol 18. To a solution of (−)-Scabronine G Methyl Ester (10 mg, 0.029 mmol) and CeCl$_3$ heptahydrate (10.8 mg, 0.029 mmol) in MeOH (5 mL) at −78° C. was added 1.5 mL of a stock solution of NaBH$_4$ (10 mg) in MeOH (10 mL). After stirring at −78° C. for 15 min, the mixture was poured into saturated NH$_4$Cl (10 mL) and extracted with Et$_2$O (2×5 mL). The combined organic extracts were dried, concentrated, and the residue purified by flash chromatography (50% EtOAc/hexanes) to afford 18 (5 mg, 50%) as a clear colorless oil: $^1$H NMR (400 MHz, CDCl$_3$) δ 5.68 (m, 1H), 4.09 (d, J=13.3 Hz, 1H), 4.00 (J=13.2 Hz, 1H), 3.81 (m, 1H), 3.70 (s, 3H), 3.13 (br d, J=12.1 Hz, 1H), 2.99 (septet, J=6.8 Hz, 1H), 2.75 (d, J=13.3 Hz, 1H), 2.68-2.43 (m, 3H), 2.32 (ddd, J=2.6, 4.1, 13.5 Hz, 1H), 2.08 (ddd, J=5.5, 9.2, 14.5 Hz, 1H), 1.85 (dt, J=4.4, 13.5 Hz, 1H), 1.68-1.47 (m, 3H), 1.33 (ddd, J=4.1, 6.7, 13.4 Hz, 1H), 1.07 (s, 3H), 1.04 (d, J=6.9 Hz, 3H), 1.02 (d, J=6.9 Hz, 3H); LRMS m/z 353.3 (M+Li$^+$), 369.2 (M+Na), 385.1 (M+K).

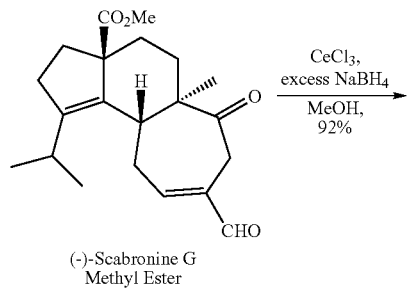

(−)-Scabronine G
Methyl Ester

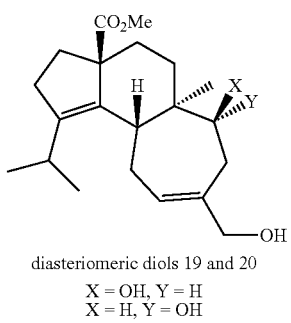

diasteriomeric diols 19 and 20
X = OH, Y = H
X = H, Y = OH

Diols 19 and 20. To a solution of (−)-Scabronine G Methyl Ester (10 mg, 0.029 mmol) and CeCl$_3$ heptahydrate (10.8 mg, 0.029 mmol in) MeOH (5 mL) at −78° C. was added solid NaBH$_4$ (8 mg, 0.21 mmol) in one portion. After 1 h at −78° C., the mixture was poured into saturated NH$_4$Cl (10 mL) and extracted with Et$_2$O (2×5 mL). The combined organic extracts were dried, concentrated, and the residue purified by flash chromatography (100% EtOAc) to afford a 2:1 mixture of diols (9.2 mg, 92%) as a clear colorless foam: Minor diastereomer: $^1$H NMR (400 MHz, CDCl$_3$) δ 5.87 (□□ J=3.0, 7.8 Hz, 1H), 4.00 (s, 1+1H), 3.67 (s, 3H), 3.29 (d, J=9.7 Hz, 1H), 2.94 (septet, J=6.8 Hz, 1H), 2.67 (m, 2H), 2.46-1.95 (m, 6H), 1.66-1.41 (m, 5H), 1.04 (d, J=6.8 Hz, 3H), 1.01 (d, J=6.8 Hz, 3H), 0.99 (s, 3H); LRMS m/z 349.4 (M+H$^+$), 371.2 (M+Na), 387.2 (M+K). Major diastereomer: $^1$H NMR (400 MHz, CDCl$_3$) δ 5.90 (dd, J=3.0, 7.8 Hz, 1H), 3.96 (s, 1+1H), 3.67 (s, 3H), 3.43 (d, J=7.7 Hz, 1H), 2.97 (septet, J=6.8 Hz, 1H), 2.61 (m, 2H), 2.43-1.91 (m, 6H), 1.71-1.12 (m, 5H), 1.04 (d, J=6.8 Hz, 3H), 0.99 (d, J=6.8 Hz, 3H), 0.94 (s, 3H); LRMS m/z 349.4 (M+H$^+$), 371.2 (M+Na), 387.2 (M+K).

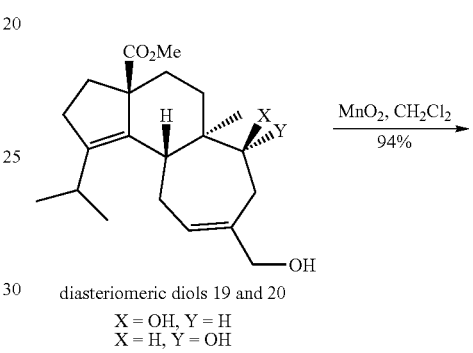

diasteriomeric diols 19 and 20
X = OH, Y = H
X = H, Y = OH

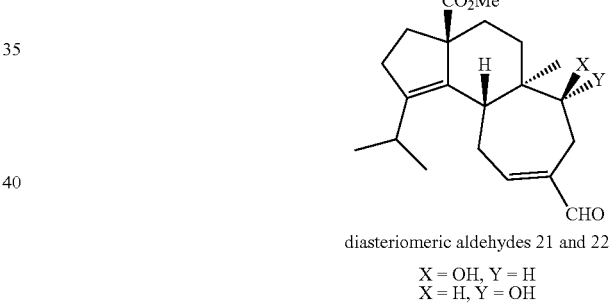

diasteriomeric aldehydes 21 and 22
X = OH, Y = H
X = H, Y = OH

Aldehydes 21 and 22. To a mixture of diols 19 and 20 (28.2 mg, 0.081 mmol) in CH$_2$Cl$_2$ (10 mL) at rt was added MnO$_2$ (56 mg, 0.65 mmol). After 2 h at rt, the mixture was filtered and the solvent removed. Purification of the residue by flash chromatography (33% EtOAc/hexanes) afforded the minor aldehyde (9.6 mg) followed by the major aldehyde (17 mg) in a combined yield of 94%: Minor diastereomer: $^1$H NMR (400 MHz, CDCl$_3$) δ 9.37 (s, 1H), 6.94 (dd, J=3.7, 8.2 Hz, 1H), 3.66 (s, 3H), 3.28 (app t, J=5.8 Hz, 1H), 2.72 (m, 2H), 2.67 (m, 3H), 2.44 (app t, J=7.6 Hz, 1H), 2.36 (br d, J=11.7 Hz, 1H), 2.20 (m, 1H), 1.99 (m, 1H), 1.69-1.38 (m, 5H), 1.07 (d, J=6.8 Hz, 3H), 1.03 (d, J=6.8 Hz, 3H), 1.01 (s, 3H); LRMS m/z 353.3 (M+Li$^+$), 369.1 (M+Na), 385.2 (M+K). Major diastereomer: $^1$H NMR (400 MHz, CDCl$_3$) δ 9.40 (s, 1H), 6.84 (dd, J=2.9, 7.8 Hz, 1H), 3.65 (s, 3H), 3.50 (br d, J=9.4 Hz, 1H), 2.92 (septet, J=6.7 Hz, 1H), 2.76 (m, 3H), 2.53 (m, 2H), 2.44 (m, 1H), 2.28 (ddd, J=2.7, 4.0, 13.4 Hz, 1H), 2.02 (m, 1H), 1.79-1.36 (m, 5H), 1.07 (d, J=6.8 Hz, 3H), 1.03 (d, J=6.8 Hz, 3H), 0.99 (s, 3H); LRMS m/z 353.3 (M+Li$^+$), 369.1 (M+Na), 385.2 (M+K).

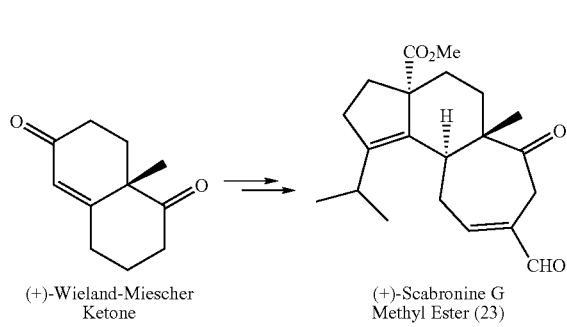

(+)-Wieland-Miescher Ketone → (+)-Scabronine G Methyl Ester (23)

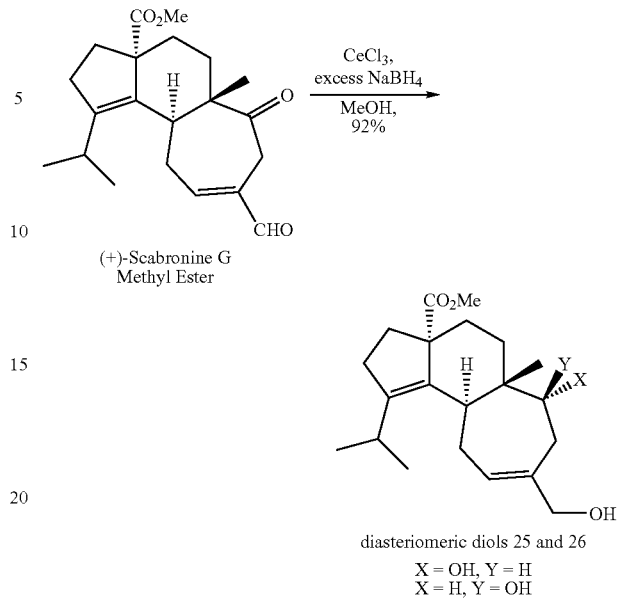

(+)-Scabronine G Methyl Ester (+)-Scabronine G Methyl Ester (23). (+)-Scabronine G Methyl Ester (23) was prepared from the (+)-Wieland-Miescher ketone following the experimental procedures outlined above for the synthesis of (−)-Scabronine G Methyl Ester. The (+)-enantiomer displayed NMR spectral data identical to that of the (−)-enantiomer.

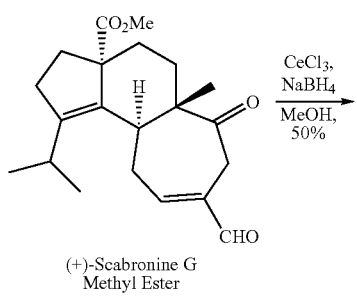

(+)-Scabronine G Methyl Ester diasteriomeric diols 25 and 26
X = OH, Y = H
X = H, Y = OH Diols 25 and 26. To a solution of (+)-Scabronine G Methyl Ester (5 mg, 0.014 mmol) and CeCl₃ heptahydrate (5.4 mg, 0.014 mmol) in MeOH (5 mL) at −78° C. was added solid NaBH₄ (4 mg, 0.11 mmol) in one portion. After 1 h at −78° C., the mixture was poured into saturated NH₄Cl (10 mL) and extracted with Et₂O (2×5 mL). The combined organic extracts were dried, concentrated, and the residue purified by flash chromatography (100% EtOAc) to afford a 2:1 mixture of diols (4.6 mg, 92%) as a clear colorless foam. These compounds displayed NMR spectral data identical to those of their enantiomers 19 and 20.

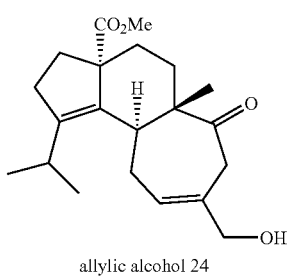

allylic alcohol 24 diasteriomeric diols 25 and 26
X = OH, Y = H
X = H, Y = OH

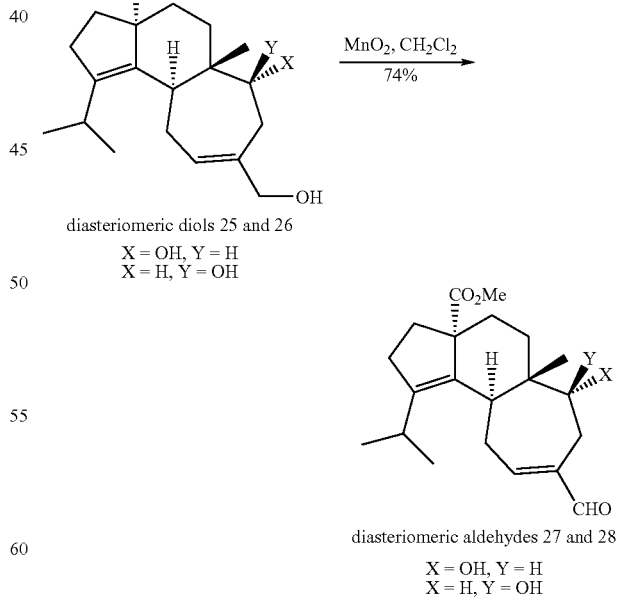

diasteriomeric aldehydes 27 and 28
X = OH, Y = H
X = H, Y = OH

Allylic alcohol 24. To a solution of (+)-Scabronine G Methyl Ester (16.6 mg, 0.048 mmol) and CeCl₃ heptahydrate (18 mg, 0.048 mmol) in MeOH (10 mL) at −78° C. was added NaBH₄ (2 mg, 0.048 mmol). After stirring at −78° C. for 15 min, the mixture was poured into saturated NH₄Cl (10 mL) and extracted with Et2O (2×5 mL). The combined organic extracts were dried, concentrated, and the residue purified by flash chromatography (50% EtOAc/hexanes) to afford 18 (8 mg, 33%) as a clear colorless oil. This compound displayed NMR spectral data identical to that of its enantiomer 18.

Aldehydes 27 and 28. To a mixture of diols 25 and 26 (5 mg, 0.014 mmol) in CH₂Cl₂ (5 mL) at rt was added as MnO₂ (20 mg, 0.23 mmol). After 2 h at rt, the mixture was filtered and the solvent removed. Purification of the residue by flash chromatography (33% EtOAc/hexanes) afforded aldehydes 27 and 28 (3.7 mg, 74%). These compounds displayed NMR spectral data identical to those of their enantiomers 21 and 22.

Example 2

Cytotoxicity Assay

Mixed neuro-glial cells were isolated from P2 SD rat pups and incubated with 2 mL of neurobasal medium containing 10 % fetal calf serum (FCS). Medium was replaced every 3 days. At day 7, culture confluence was assessed (>80%), and (+)-scabronine G (SPWII-46), (−)-scabronine G (SPWI-174b), an analog of (+)-scabronine G (SPWII-49b, SPWII-49a, or SPWII-50), or vehicle (5 μL of DMSO) as a control was then incubated at the indicated concentration with the cells for 24 hours. After 24 hours, the medium was collected and diluted, and LDH activity was measured. A positive control was also performed using a cell culture incubated with Triton-based lysis buffer for 30 minutes. All cell culture plates were also visualize for cell vitality.

For analog SPWI-174b, the cytotoxic effect was comparable to the vehicle control up to approximately 100 μM. See FIG. 6. Analog SPWII-49b was the least toxic of the compounds tested using the LDH release cytotoxicity assay. See FIG. 6.

Example 3

NGF Assay and Neurite Outgrowth

Figure 7:
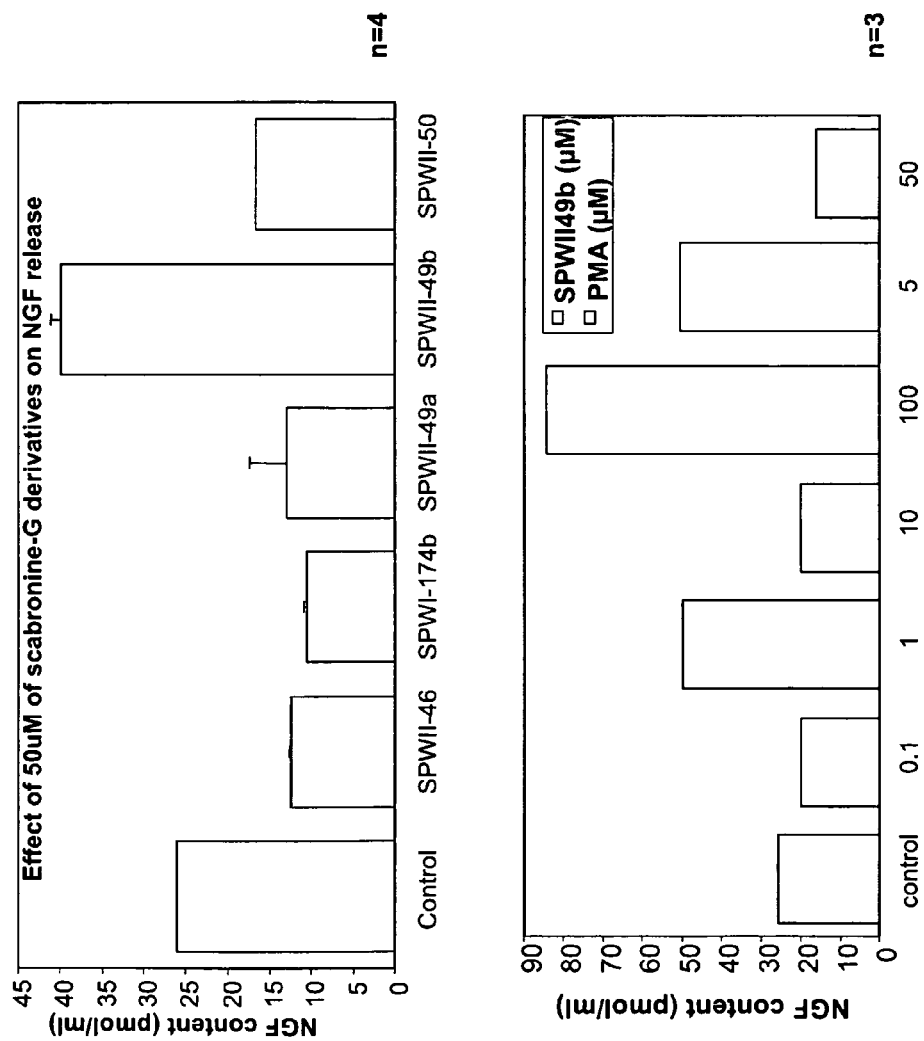
FIG. 7 shows the effect of scabronine G and various analogs depicted in FIG. 5A on the release of NGF.

Mixed neuro-glial cells were isolated from P2 SD rat pups and incubated with 2 mL of neurobasal medium containing 10 % fetal calf serum (FCS). Medium was replaced every 3 days. At day 5-6 when culture confluence was at >80%, the cells were trypsinized (5 minutes at 37° C.) and recultured at a ratio of 1:2. When 50% confluence was reached, 1 mL of medium was removed, and (+)-scabronine G (SPWII-46), (−)-scabronine G (SPWI-174b), an analog of (+)-scabronine G (SPWII-49b, SPWII-49a, or SPWII-50), or vehicle (5 μL of DMSO) as a control was added to the cells at a final concentration of 50 μM for 24 hours. In addition, a series of concentrations (0.1 μM, 1 μM, 10 μM, and 100 μM) was tested for scabronine G analog SPWII-49b. Media was collected from the cells after 24 hours, and 200 μL of the medium was used to determine the NGF content in the medium by ELISA assay. Medium was incubated in ELISA wells coated with Ms anti-NGF antibodies. The next day NGF levels were assessed based on a standard curve. See FIG. 7 Positive controls were performed with cell cultures incubated with phorbol 12β-myristate 13α-acetate (PMA) at 5 μM and 50 μM. *Brain Res.* 570:316-22, 1990; incubated herein by reference.

Figure 8A:
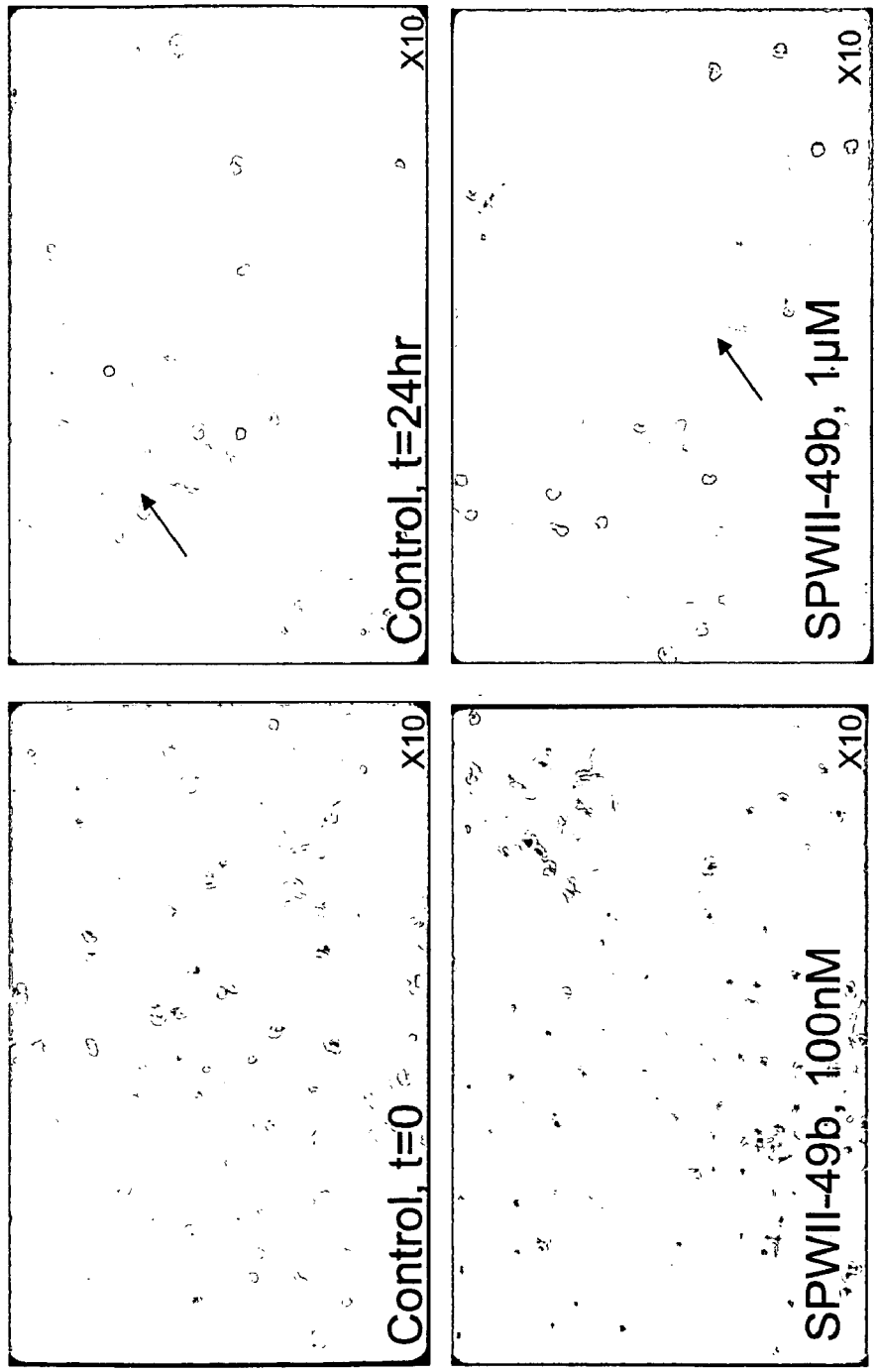
FIGS. 8A and 8B shows the effect of scabronine G analog (SPWII-49b) on neurite outgrowth in mixed neuro-glial cell culture at various concentrations as compared to a vehicle control.
Figure 8B:
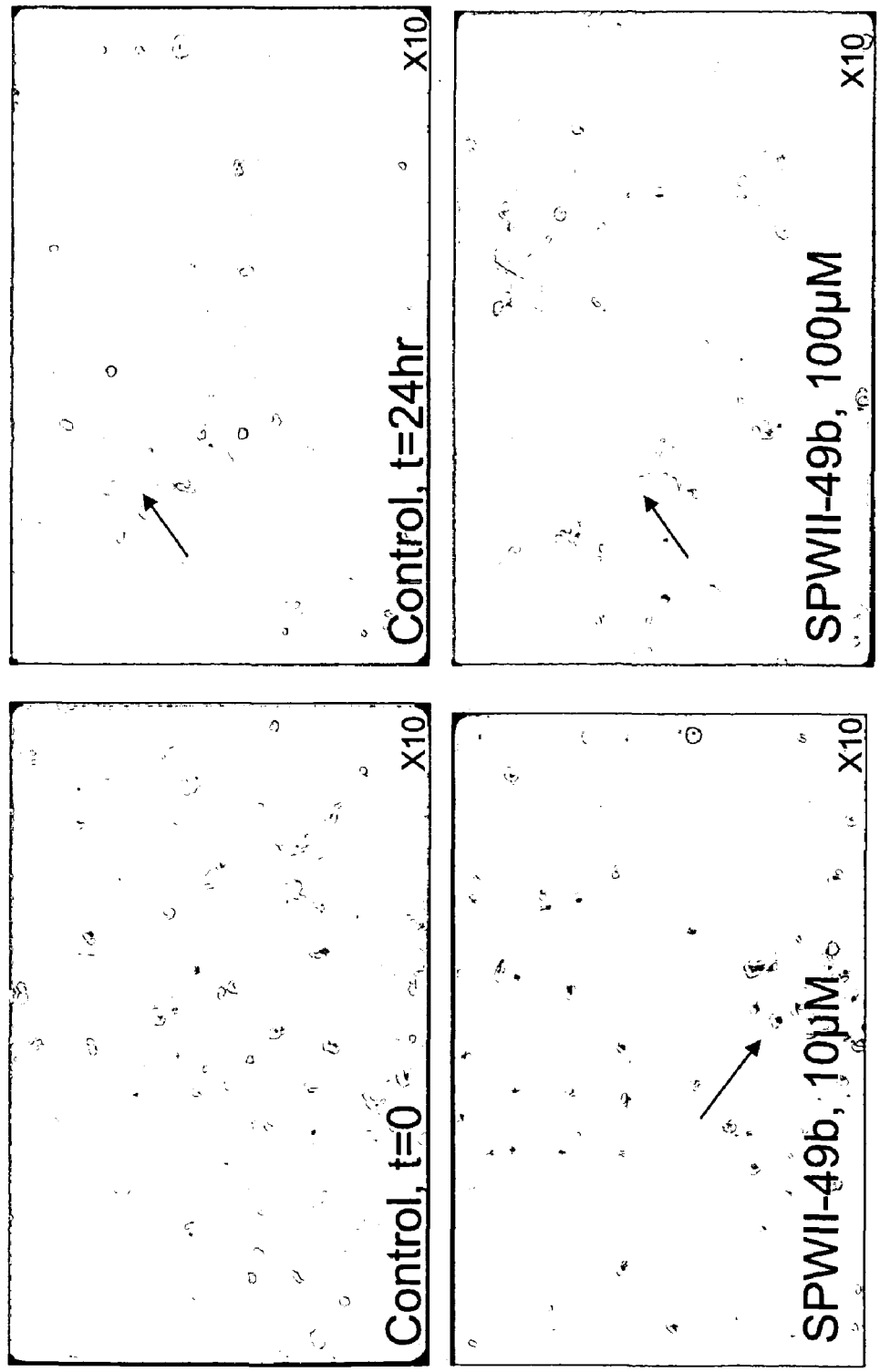

The cells incubated with compound were also visualized for cell vitality and neurite growth. See FIGS. 8A and 8B.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:
1. A compound of the formula

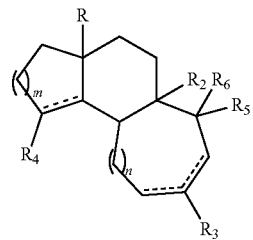

wherein
each dashed line independently represents the absence of a bond or a carbon-carbon bond of a carbon-carbon double bond;
m is an integer between 0 and 3, inclusive;
n is an integer between 0 and 2, inclusive;
R is C(=O)R$_1$ or CN; wherein
R$_1$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; substituted or unsubstituted, branched or unbranched heteroaryl; —OR$_A$; —OH; —C(=O)R$_A$; —CO$_2$R$_A$; —CN; —SCN; —SR$_A$; —SH; —N(R$_A$)$_2$; —NHR$_A$; —NH$_2$; or —C(R$_A$)$_3$; wherein each occurrence of R$_A$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
R$_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_B$; —OH; —C(=O)R$_B$; —CO$_2$R$_B$; —CN; —SCN; —SR$_B$; —SH; —SOR$_B$; —SO$_2$R$_B$; —NO$_2$; —N(R$_B$)$_2$; —NHR$_B$; —NH$_2$; —NHC(=O)R$_B$; —OC(=O)R$_B$; or —C(R$_B$)$_3$; wherein each occurrence of R$_B$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
R$_3$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_C$; —OH; —C(=O)R$_C$; —CO$_2$R$_C$; —CN; —SCN; —SR$_C$; —SH; —SOR$_C$; —SO$_2$R$_C$; —NO$_2$; —N(R$_C$)$_2$; —NHR$_C$; —NH$_2$; —NHC(=O)R$_C$; —OC(=O)R$_C$; or —C(R$_C$)$_3$; wherein each occurrence of R$_C$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R₄ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; —OH; —C(=O)R$_D$; —CO$_2$R$_D$; —CN; —SCN; —SR$_D$; —SH; —SOR$_D$; —SO$_2$R$_D$; —NO$_2$; —N(R$_D$)$_2$; —NHR$_D$; —NH$_2$; —NHC(=O)R$_D$; —OC(=O)R$_D$; or —C(R$_D$)$_3$; wherein each occurrence of R$_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_E$; —OH; —C(=O)R$_E$; —CO$_2$R$_E$; —CN; —SCN; —SR$_E$; —SH; —SOR$_E$; —SO$_2$R$_E$; —NO$_2$; —N(R$_E$)$_2$; —NHR$_E$; —NH$_2$; —NHC(=O)R$_E$; —OC(=O)R$_E$; or —C(R$_E$)$_3$; wherein each occurrence of R$_E$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_6$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_F$; —OH; —C(=O)R$_F$; —CO$_2$R$_F$; —CN; —SCN; —SR$_F$; —SH; —SOR$_F$; —SO$_2$R$_F$; —NO$_2$; —N(R$_F$)$_2$; —NHR$_F$; —NH$_2$; —NHC(=O)R$_F$; —OC(=O)R$_F$; or —C(R$_F$)$_3$; wherein each occurrence of R$_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

R$_5$ and R$_6$ may be take together to form =O, =S, =NR$_E$; =C(R$_E$)$_2$, or a carbocyclic or heterocyclic moiety; or a therapeutically acceptable salt thereof;

wherein at least one of m and n is 1.

2. The compound of claim 1 of formula:

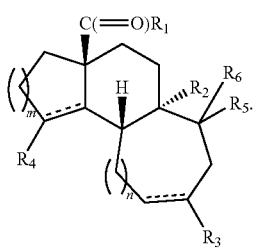

3. The compound of claim 1 of formula:

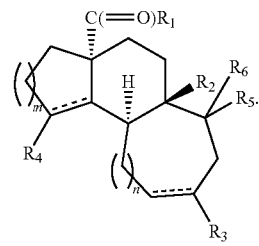

4. The compound of claim 1 of formula:

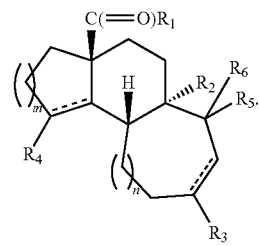

5. The compound of claim 1 of formula:

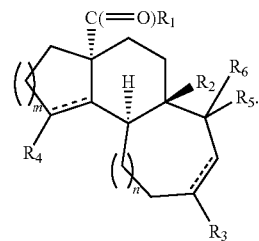

6. The compound of claim 1 of formula:

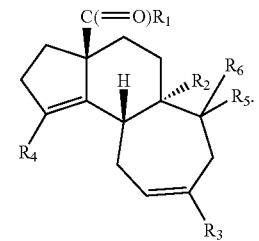

7. The compound of claim 1 of formula:

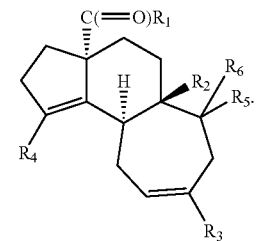

8. The compound of claim 1 of formula:
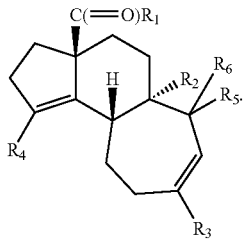
9. The compound of claim 1 of formula:
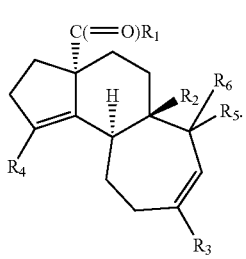
10. The compound of claim 1 of any one of the formulae:
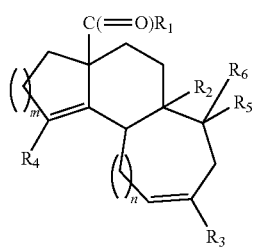 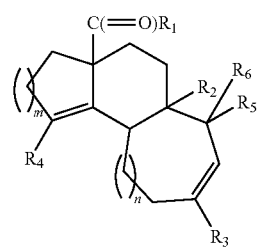
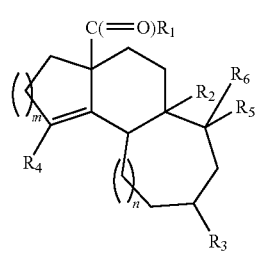 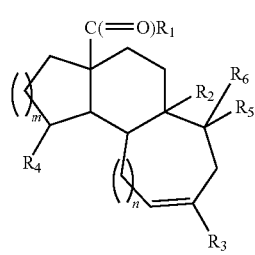
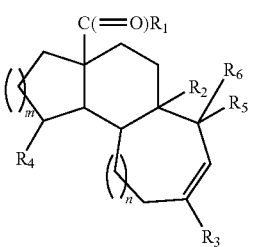 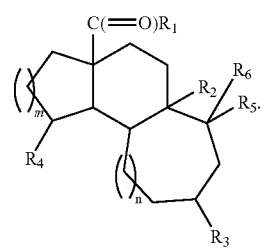
11. The compound of claim 1, having the formula:
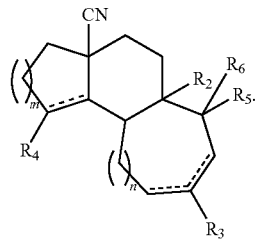
12. The compound of claim 1 of any one of the formulae:
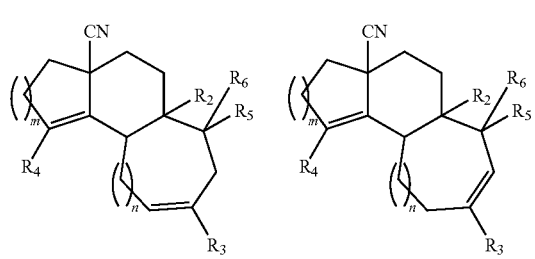
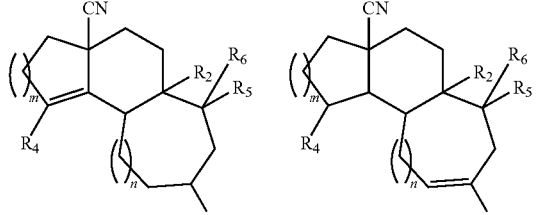
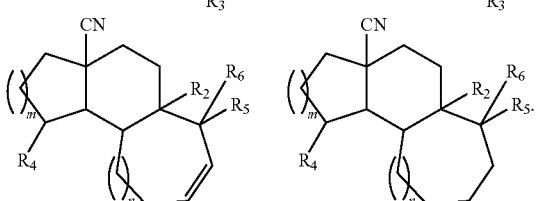
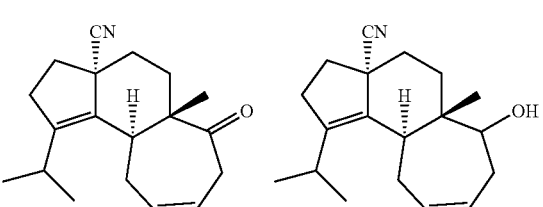
13. The compound of claim 1 of one of the formulae:
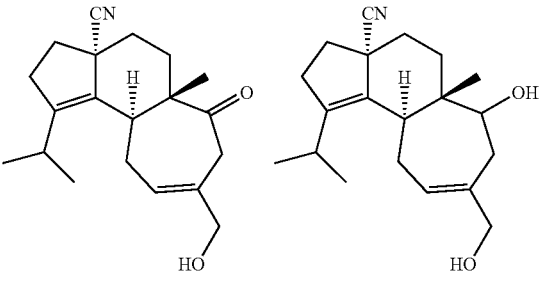

-continued

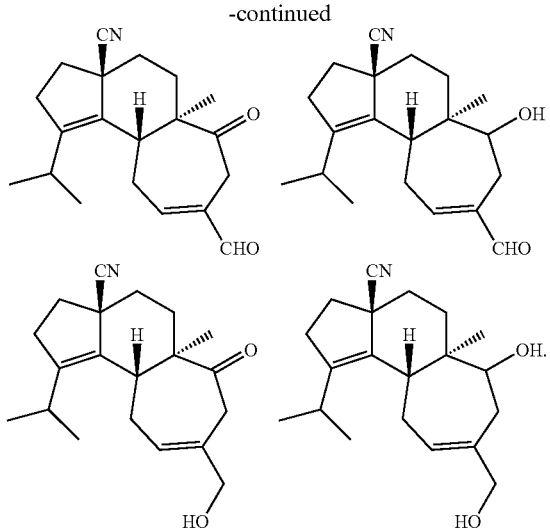

14. The compound of claim 1, wherein m is 1.
15. The compound of claim 1, wherein m is 2.
16. The compound of claim 1, wherein m is 0.
17. The compound of claim 1, wherein n is 1.
18. The compound of claim 1, wherein n is 2.
19. The compound of claim 1, wherein n is 0.
20. The compound of claim 1, wherein m and n are both 1.
21. The compound of claim 1, wherein R is C(=O)R$_1$.
22. The compound of claim 21, wherein R$_1$ is hydrogen.
23. The compound of claim 21, wherein R$_1$ is —OR$_A$.
24. The compound of claim 21, wherein R$_1$ is —OH.
25. The compound of claim 21, wherein R$_1$ is —OR$_A$, wherein R$_A$ is C$_1$-C$_6$ alkyl.
26. The compound of claim 21, wherein R$_1$ is —OMe.
27. The compound of claim 21, wherein R$_1$ is —N(R$_A$)$_2$.
28. The compound of claim 1, wherein R$_2$ is hydrogen.
29. The compound of claim 1, wherein R$_2$ is C$_1$-C$_6$ alkyl.
30. The compound of claim 1, wherein R$_2$ is methyl.
31. The compound of claim 1, wherein R$_3$ is hydrogen.
32. The compound of claim 1, wherein R$_3$ is C$_1$-C$_6$ alkyl.
33. The compound of claim 1, wherein R$_3$ is —CHO.
34. The compound of claim 1, wherein R$_3$ is acyl.
35. The compound of claim 1, wherein R$_3$ is —CH$_2$OR$_C$.
36. The compound of claim 1, wherein R$_3$ is —CH$_2$OR$_C$, wherein R$_C$ is hydrogen, C$_1$-C$_6$ alkyl, substituted or unsubstituted aryl, or substituted or unsubstituted heteroaryl.
37. The compound of claim 1, wherein R$_3$ is —CH$_2$OH.
38. The compound of claim 1, wherein R$_4$ is hydrogen.
39. The compound of claim 1, wherein R$_4$ is C$_1$-C$_6$ alkyl.
40. The compound of claim 1, wherein R$_4$ is methyl.
41. The compound of claim 1, wherein R$_4$ is ethyl.
42. The compound of claim 1, wherein R$_4$ is propyl.
43. The compound of claim 1, wherein R$_4$ is iso-propyl.
44. The compound of claim 1, wherein R$_4$ is substituted or unsubstituted aryl.
45. The compound of claim 1, wherein R$_4$ is substituted or unsubstituted heteroaryl.
46. The compound of claim 1, wherein R$_4$ is acyl.
47. The compound of claim 1, wherein R$_5$ is hydrogen.
48. The compound of claim 1, wherein R$_5$ is —OR$_E$.
49. The compound of claim 1, wherein R$_5$ is —OH.
50. The compound of claim 1, wherein R$_6$ is hydrogen.
51. The compound of claim 1, wherein R$_6$ is —OR$_F$.
52. The compound of claim 1, wherein R$_6$ is —OH.
53. The compound of claim 1, wherein R$_5$ is —OH; and R$_6$ is hydrogen.
54. The compound of claim 1, wherein R$_5$ is hydrogen; and R$_6$ is —OH.
55. The compound of claim 1, wherein R$_5$ and R$_6$ are taken together to be =O.
56. The compound of claim 1, wherein R$_5$ and R$_6$ are taken together to be =S.
57. The compound of claim 1, wherein R$_5$ and R$_6$ are taken together to be =C(R$_E$)$_2$.
58. The compound of claim 1, wherein R$_5$ and R$_6$ are taken together to be =NR$_E$.
59. The compound of claim 1, wherein R$_5$ and R$_6$ are taken together to be a carbocyclic or heterocyclic moiety optionally substituted.
60. The compound of claim 1 of one of the formulae:

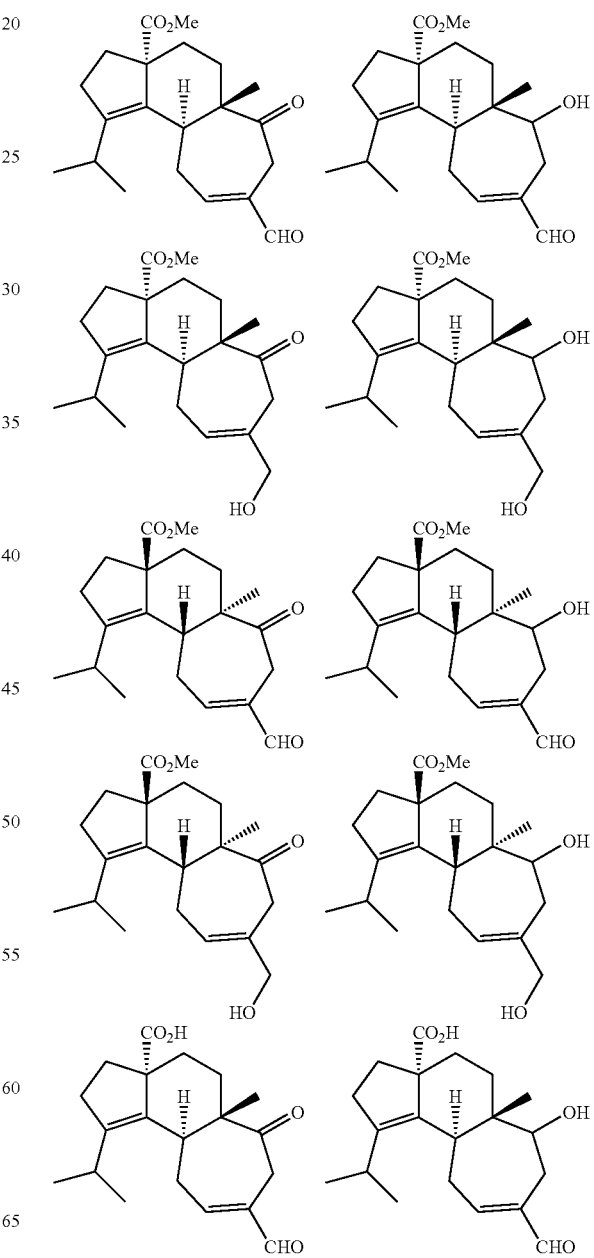

-continued
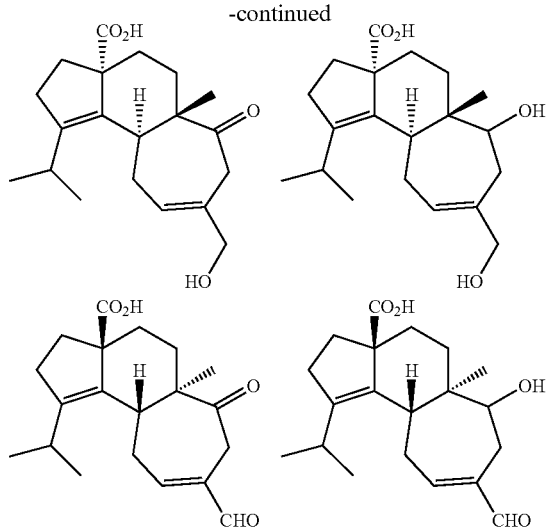
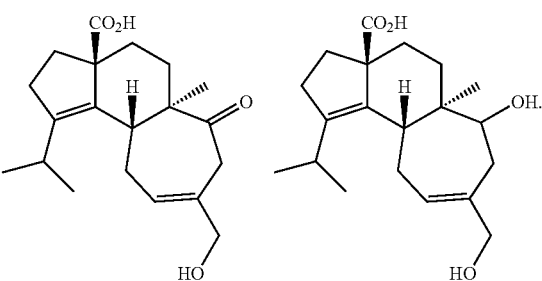
61. A pharmaceutical composition comprising a compound of claim 1 and a pharmaceutically acceptable excipient.
* * * * *

UNITED STATES PATENT AND TRADEMARK OFFICE
CERTIFICATE OF CORRECTION

| | | |
|---|---|---|
| PATENT NO. | : 7,910,623 B2 | Page 1 of 1 |
| APPLICATION NO. | : 12/017951 | |
| DATED | : March 22, 2011 | |
| INVENTOR(S) | : Samuel J Danishefsky | |

It is certified that error appears in the above-identified patent and that said Letters Patent is hereby corrected as shown below:

Specification

In column 1, beginning at line 6 and ending at line 9, please delete:

"The work described herein was supported, in part, by grants from the National Institutes of Health (Grant HL25848). The United States government may have certain rights in the invention."

and insert:

-- This invention was made with government support under grant number HL025848 awarded by National Institutes of Health. The government has certain rights in the invention. --

Signed and Sealed this
Seventeenth Day of May, 2016

Michelle K. Lee
*Director of the United States Patent and Trademark Office*